(12) United States Patent
Bischof et al.

(10) Patent No.: US 7,264,608 B2
(45) Date of Patent: Sep. 4, 2007

(54) MANUAL PROCESSING SYSTEMS AND METHODS FOR PROVIDING BLOOD COMPONENTS CONDITIONED FOR PATHOGEN INACTIVATION

(75) Inventors: Daniel F. Bischof, Bull Valley, IL (US); Ying-Cheng Lo, Green Oaks, IL (US); Daniel Lynn, Spring Grove, IL (US); Bryan J Blickhan, Zion, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 10/008,361

(22) Filed: Dec. 5, 2001

(65) Prior Publication Data
US 2003/0104349 A1 Jun. 5, 2003

(51) Int. Cl.
*A61M 29/00* (2006.01)
*A61M 35/00* (2006.01)

(52) U.S. Cl. ............... 604/96.01; 604/4.01; 604/6.01; 604/403; 604/408; 222/94

(58) Field of Classification Search ............... 604/4.01, 604/6.01, 6.04, 6.07, 6.15, 403, 408, 410, 604/416, 903, 6.02, 6.03, 6.09, 6.1, 6.16, 604/19, 27, 30–34, 93.01, 115, 128, 158, 604/246, 168.02, 168.01, 167.01, 167.03, 604/167.05, 167.04, 257, 258, 262, 264, 604/523, 537, 317, 327, 96.01; 128/DIG. 24; 220/62.11–62.22; 222/92, 94, 129, 130, 222/132–135, 142.1, 206, 207, 566, 567, 222/569, 572, 57, 71, 145.7–145.8, 189.06, 222/189.11, 192, 630, 211, 215, 251, 323, 222/330, 386, 387, 544, 545; 435/2, 173.1, 435/173.3, 235.1, 236, 238, 262, 267, 269, 435/800, 814; 424/607, 610, 611, 661, 663; 514/1, 2, 777, 832, 833
See application file for complete search history.

(56) References Cited

U.S. PATENT DOCUMENTS

| | | | |
|---|---|---|---|
| 4,322,298 A | 3/1982 | Persidsky | |
| 4,748,120 A | 5/1988 | Wiesehahn | |
| 4,767,541 A | 8/1988 | Wisdom | |
| 4,880,548 A | 11/1989 | Pall et al. | |
| 4,936,998 A | 6/1990 | Nishimura et al. | |
| 5,056,568 A | 10/1991 | DiGianfilippo et al. | |
| 5,089,146 A | 2/1992 | Carmen et al. | |
| 5,100,564 A | 3/1992 | Pall et al. | |
| 5,102,407 A | 4/1992 | Carmen et al. | |
| 5,128,048 A * | 7/1992 | Stewart et al. | 210/749 |
| 5,152,905 A | 10/1992 | Pall et al. | |
| 5,167,656 A * | 12/1992 | Lynn | 604/409 |
| 5,236,716 A | 8/1993 | Carmen et al. | |

(Continued)

FOREIGN PATENT DOCUMENTS

| | | |
|---|---|---|
| EP | 0 442 114 A2 | 8/1991 |
| EP | 02804701 | 10/2005 |
| WO | WO90/00059 A1 | 1/1990 |
| WO | WO98/28057 A1 | 7/1998 |

*Primary Examiner*—Tatyana Zalukaeva
*Assistant Examiner*—Phil Wiest
(74) *Attorney, Agent, or Firm*—Cook, Alex, McFarron, Manzo, Cummings & Mehler, Ltd.

(57) ABSTRACT

Systems and methods manually process blood and blood components in sterile, closed environments, which further condition the blood components for subsequent pathogen inactivation processes. The systems and methods mate the manual collection of random donor platelet units with the creation of larger therapeutic doses of platelets targeted to undergo pathogen inactivation prior to long term storage and/or transfusion.

5 Claims, 13 Drawing Sheets

U.S. PATENT DOCUMENTS

| | | |
|---|---|---|
| 5,269,946 A * | 12/1993 | Goldhaber et al. ......... 210/767 |
| 5,364,526 A | 11/1994 | Matkovich et al. |
| 5,399,268 A | 3/1995 | Pall et al. |
| 5,536,238 A | 7/1996 | Bischof |
| 5,660,731 A | 8/1997 | Piechocki et al. |
| 5,690,815 A | 11/1997 | Krasnoff et al. |
| RE35,804 E | 5/1998 | Stewart |
| 5,899,874 A | 5/1999 | Jonsson |
| 5,935,092 A | 8/1999 | Sun et al. |
| 6,063,624 A | 5/2000 | Kandler et al. |
| 6,133,460 A | 10/2000 | Nerio et al. |
| 6,190,855 B1 | 2/2001 | Herman et al. |
| 6,258,577 B1 | 7/2001 | Goodrich, Jr. et al. |
| 6,268,120 B1 | 7/2001 | Platz et al. |
| 6,277,337 B1 | 8/2001 | Goodrich, Jr. et al. |
| 6,326,197 B1 * | 12/2001 | Kandler et al. .............. 435/372 |
| 6,422,397 B1 * | 7/2002 | Lynn et al. .................. 210/489 |
| 6,566,046 B2 * | 5/2003 | Lin et al. ........................ 435/2 |
| 2001/0052497 A1 * | 12/2001 | Blickhan et al. ............ 210/669 |

\* cited by examiner

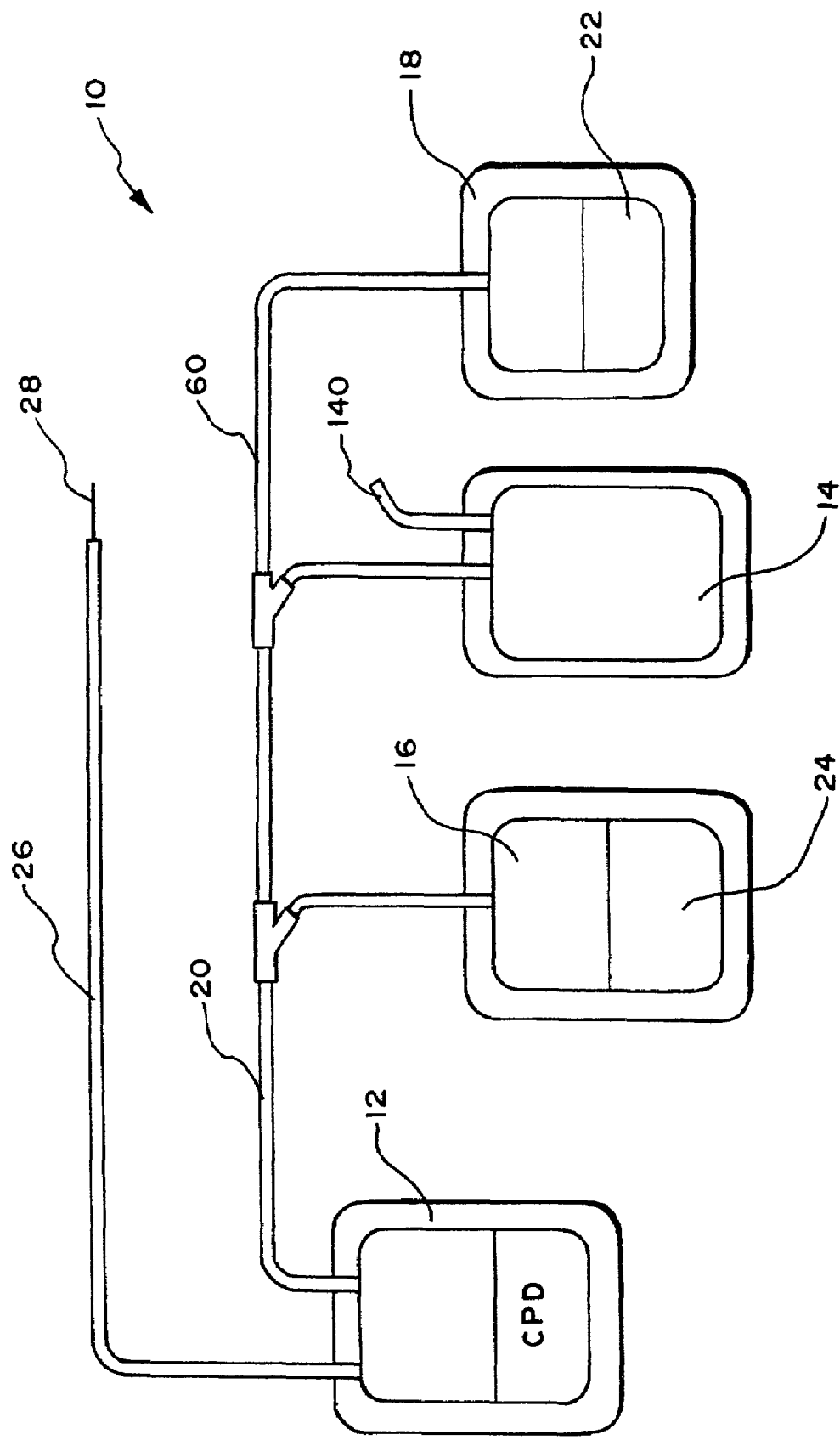

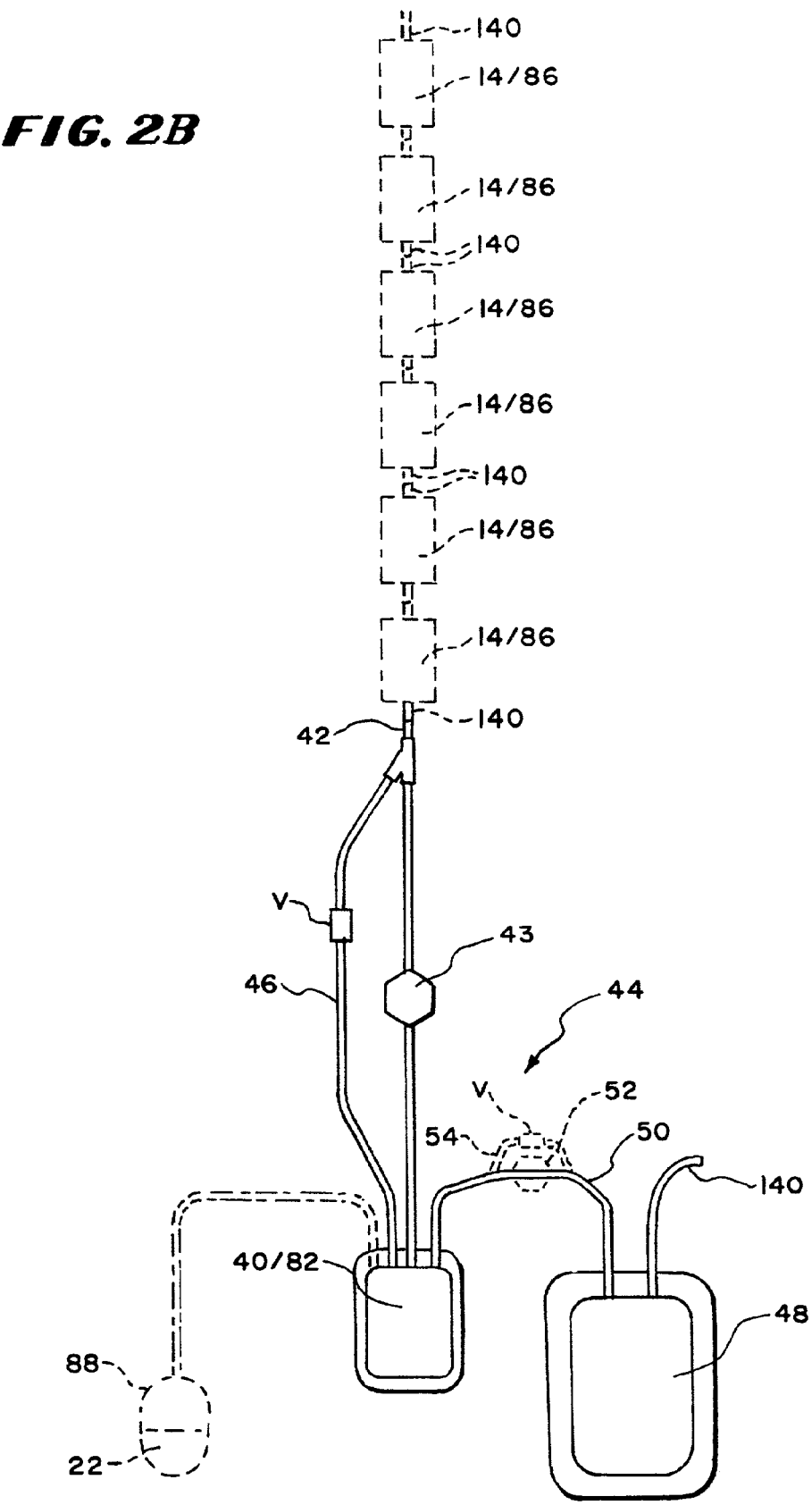

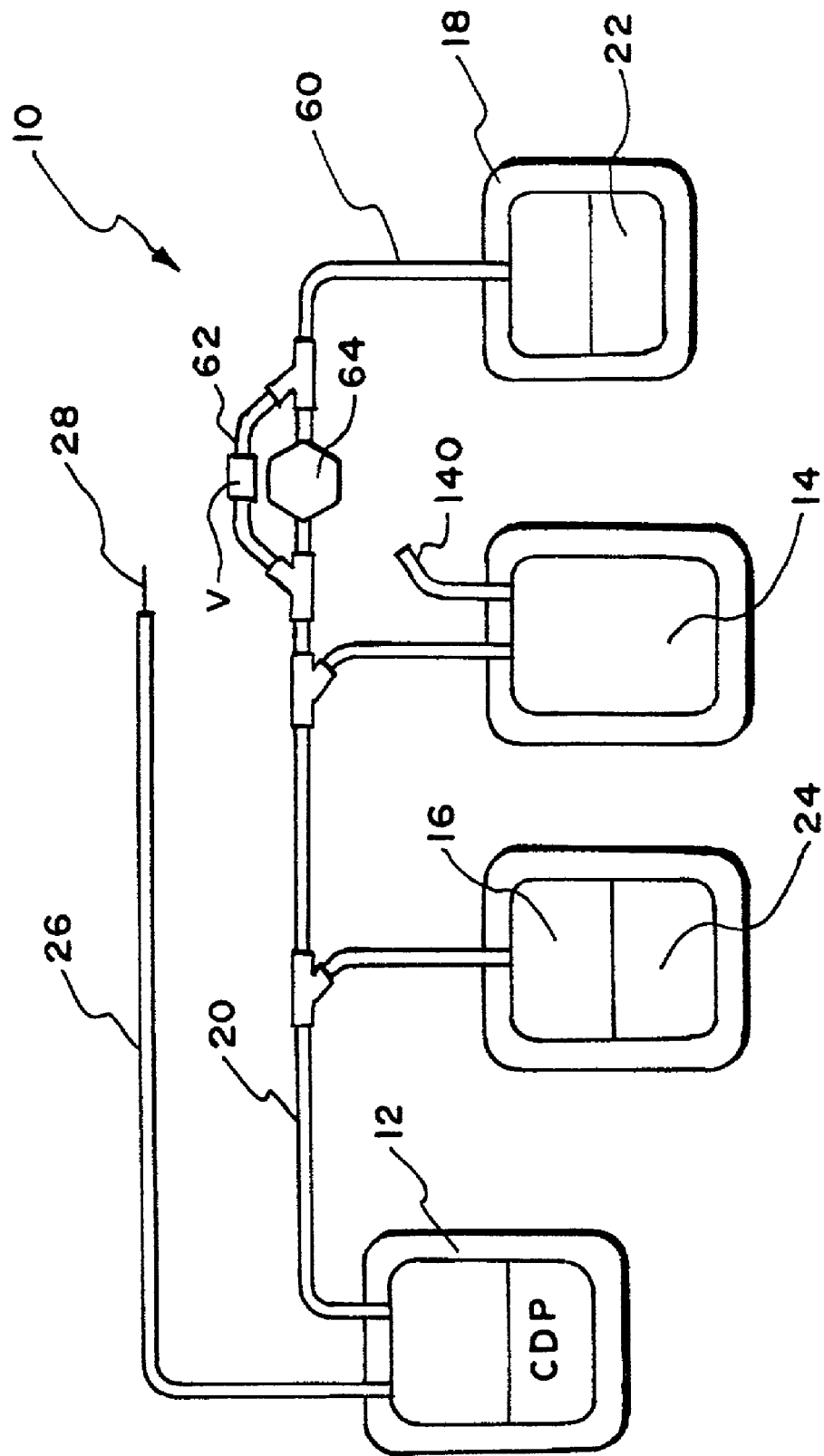

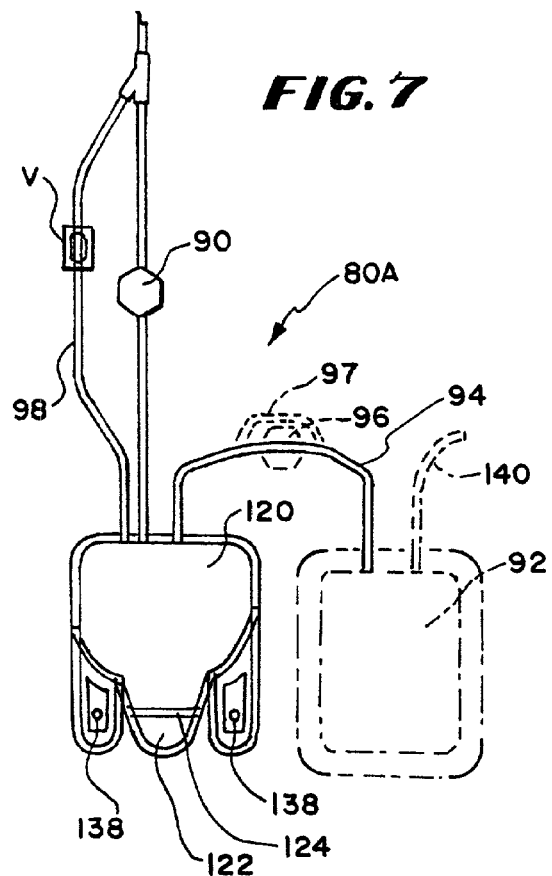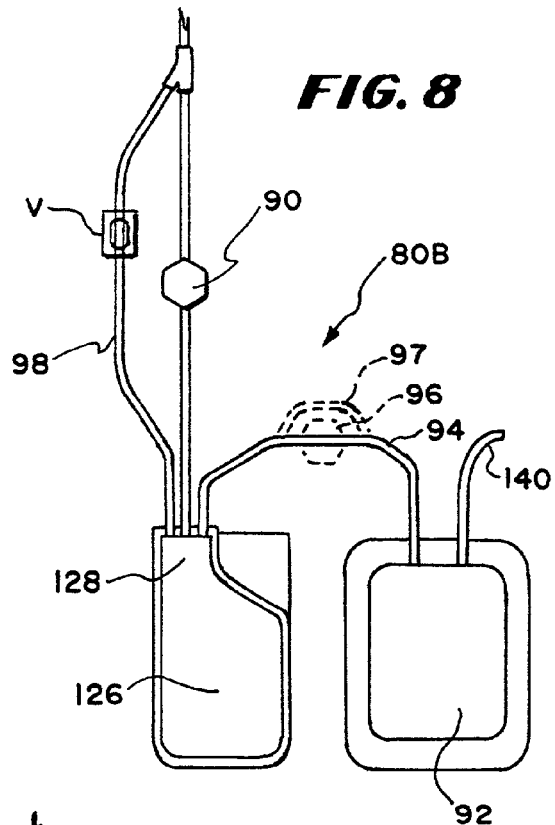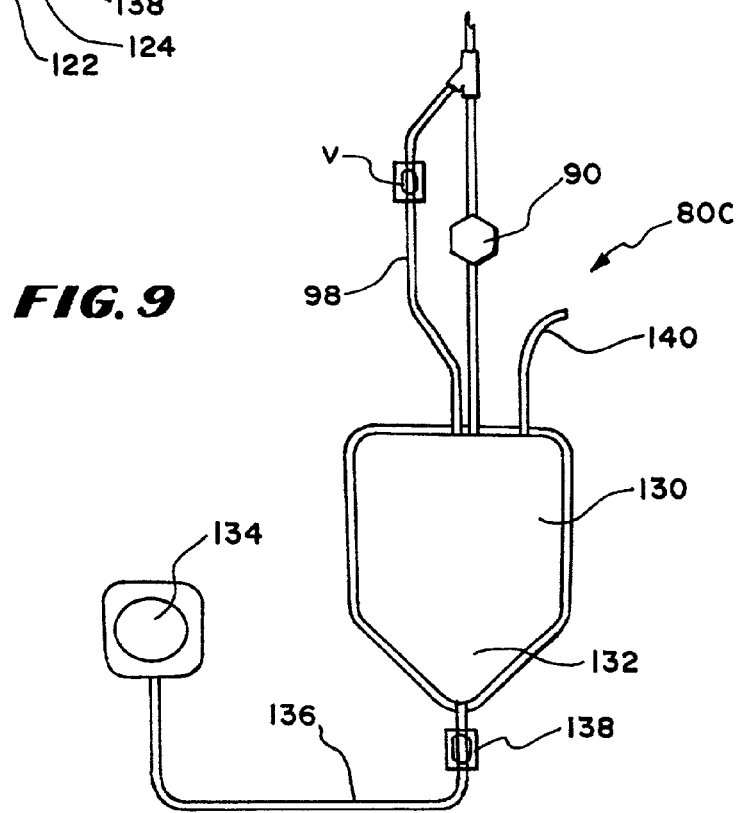

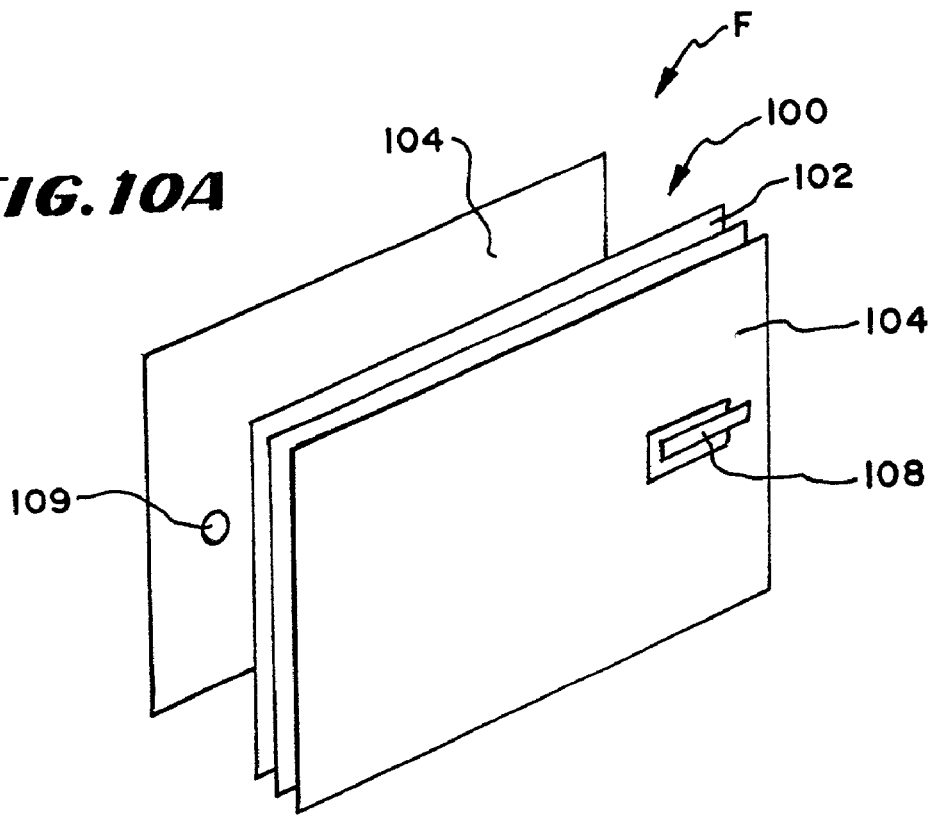
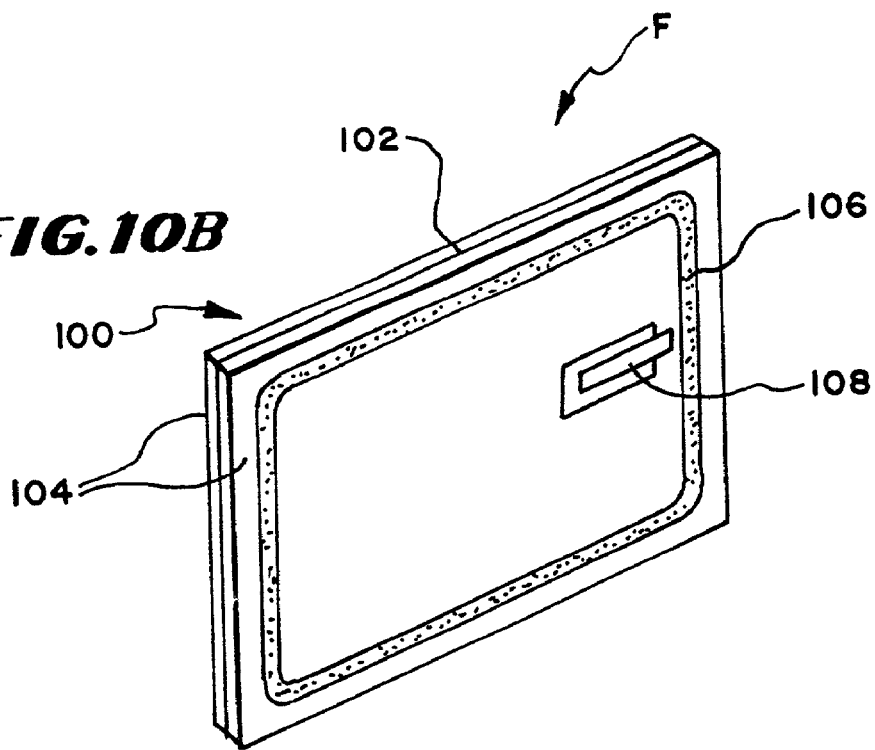

MANUAL PROCESSING SYSTEMS AND METHODS FOR PROVIDING BLOOD COMPONENTS CONDITIONED FOR PATHOGEN INACTIVATION

FIELD OF THE INVENTION

The invention generally relates to the processing of whole blood and its components for storage, fractionation, and transfusion.

BACKGROUND OF THE INVENTION

The clinically proven components of whole blood include, e.g., red blood cells, which can be used to treat chronic anemia; plasma, which can be used as a blood volume expander or which can be fractionated to obtain Clotting Factor VIII-rich cryoprecipitate for treatment of hemophilia; and concentrations of platelets, used to control thrombocytopenic bleeding.

Along with the growing demand for these blood components, there is also a growing expectation for purity of the blood product. Before storing blood components such as red blood cells or platelets for later transfusion, it is believed to be desirable to minimize the presence of impurities or other materials that may cause undesired side effects in the recipient.

For example, it is generally considered desirable to remove leukocytes from such blood components before storage, or at least before transfusion. It is also believed beneficial that potential blood-born pathogens, e.g., free viruses and bacteria, be inactivated from blood components prior to transfusion, e.g., through the use of photoactive and non-photoactive chemical reactions.

SUMMARY OF THE INVENTION

The invention provides systems and methods for manually processing blood and blood components in sterile, closed environments, which further condition the blood components for subsequent pathogen inactivation processes. The systems and methods make possible optional new systems and methods, which mate the manual collection of random donor platelet units with the creation of larger therapeutic doses of platelets targeted to undergo pathogen inactivation prior to long term storage and/or transfusion.

DESCRIPTION OF THE DRAWINGS

FIG. 1 is a blood processing system accommodating the mixing of a platelet additive solution to a platelet component within an integral, sterile closed system, to thereby condition the platelet component for pathogen inactivation;

FIGS. 2A and 2B are kits for pooling random donor units of platelet components premixed with a platelet additive solution;

FIG. 3 is a blood processing system accommodating the mixing of a platelet additive solution to a platelet component within an integral, sterile closed system, as well as accommodating the filtering of the mixture to remove leukocytes, to thereby condition the platelet component for pathogen inactivation in a leukocyte-reduced state;

FIGS. 7 to 9 are views of alternative embodiments of a pooling container that can be incorporated into the pooling kit shown in either FIGS. 2A/2B or FIG. 6 and that augment the isolation and removal of residual red blood cells from the pooled platelet component;

FIG. 10A is an exploded perspective view of a filter for removing leukocytes from a platelet or red blood cell component, which is usable in association with the systems shown in FIGS. 2 to 6;

FIG. 10B is an assembled perspective view of the filter shown in FIG. 10A;

Figure 2A:
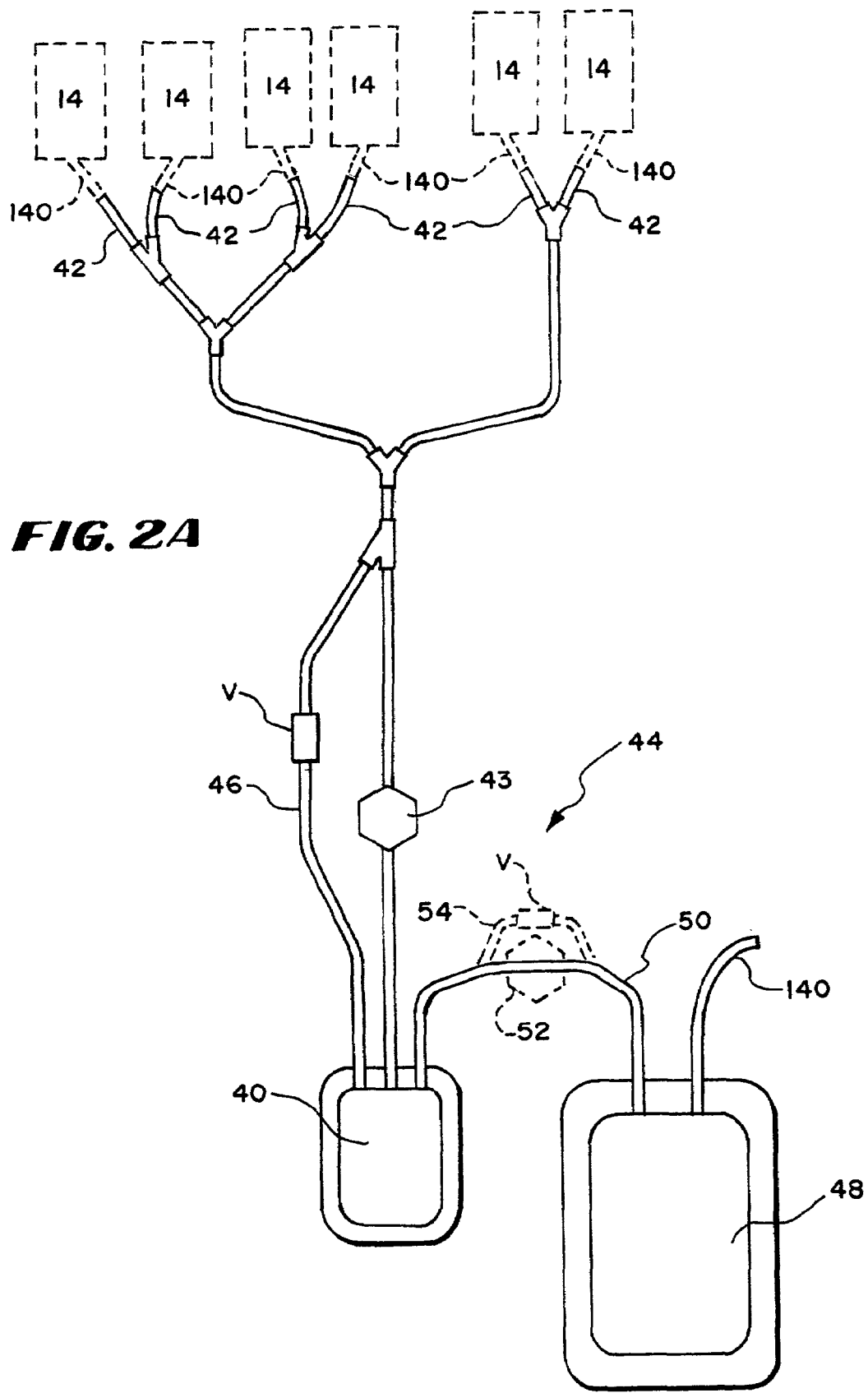

The invention is not limited to the details of the construction and the arrangements of parts set forth in the following description or shown in the drawings. The invention can be practiced in other embodiments and in various other ways. The terminology and phrases are used for description and should not be regarded as limiting.

DESCRIPTION OF THE PREFERRED EMBODIMENTS

FIG. 1 shows a manually manipulated blood collection and storage system 10 that embodies features of the invention. The system 10 is intended to be a disposable, single use item.

The system 10, once sterilized, constitutes an integral, sterile, "closed" system, as judged by the applicable standards. In the United States, blood storage procedures are subject to regulation by the government. The maximum storage periods for the blood components collected in these systems are specifically prescribed. For example, in the United States, whole blood components collected in an "open" (i.e., non-sterile) system must, under governmental rules, be transfused within twenty-four hours and in most cases within six to eight hours. By contrast, when whole blood components are collected in a "closed" (i.e., sterile) system the red blood cells can be stored in a prescribed cold environment up to forty-two days (depending upon the type of anticoagulant and storage medium used), plasma may be frozen and stored for even longer periods, and platelet concentrate may stored at room temperature conditions for up to five days.

The system 10 includes a primary blood processing container 12. In use, the primary container 12 receives a unit of whole blood for centrifugal separation through integrally attached donor tubing 26 and phlebotomy needle 28. In the embodiment illustrated in FIG. 1, the primary container 12 carries a suitable anticoagulant, e.g., CPD.

The system 10 also includes at least one transfer container 14, which is integrally attached to the primary container 12 by an array of flexible transfer tubing 20. In use, the transfer container 14 receives a blood component separated by centrifugation in the primary container 12. Desirably, the transfer container 14 also serves as a storage container for one blood component at the end of processing.

The system 10 also includes at least one additive solution container 18, which is integrally attached to the primary container 12 by the flexible transfer tubing array 20. The additive solution container 18 holds an additive solution for the blood component that is ultimately stored in transfer container 14. In use, the additive solution is mixed with the blood component at some point during blood processing. The composition of the additive solution can vary according to the type of blood component with which it is mixed.

Desirably, the transfer container 14 is intended to store a platelet component, and, in particular, a platelet concentrate containing a residual amount of plasma, which is derived by centrifugation of platelet-rich plasma.

It is desirable that the platelet concentrate in the container 14 be in a condition that would facilitate a subsequent pathogen inactivation process. Thus, the solution container 18 desirably includes an additive solution 22 that specially conditions the platelet concentrate for pathogen inactivation in terms of, e.g., desired viscosity and light adsorption properties (to aid the transmission of the light energy typically used in a photoactive pathogen inactivation process) and/or desired physiologic conditions, such as pH, which are conducive to effective pathogen inactivation. The additive solution 22 also desirably conditions the platelet concentrate for long-term storage after pathogen inactivation, by providing the proper mix of nutrients and buffers to sustain platelet metabolism during storage.

To achieve these objectives, the solution container 18 includes an additive solution 22 that desirably comprises a synthetic media for use in conjunction with the pathogen inactivation of platelets. The synthetic media comprises an aqueous solution (e.g., phosphate buffered, aqueous salt solutions) other than those found as natural fluids (e.g., plasma, serum, etc.). The synthetic media is added to the platelet concentrate, which optionally includes a residual volume of plasma, so that, after processing, the platelet concentrate resides in a mixture of the synthetic media and plasma. Depending upon the particular formulation of the media 22, it is desirable that a prescribed ratio between the media 22 and residual plasma exists in the mixture.

In a preferred embodiment, the desired mixture of the synthetic media 22 and plasma conditions the platelet concentrate for decontamination of pathogens in the presence of a desired volume of a pathogen inactivating compound, which is added to the platelet concentrate and additive solution mixture after processing in the system 10. The pathogen inactivating compound can comprise a nucleic acid binding compound, which is desirably selected from the group comprising furocoumarins. In a preferred embodiment, the furocoumarin is a psoralen that is activated by a photoactivation device, such as disclosed in U.S. Pat. Nos. 5,578,736 and 5,593,823. Most preferred, the psoralen comprises 5'-(4-amino-2-oxa) butyl-4,5',8-trimethylpsoralen (also referred to as S-59), present in concentrations of approximately 100 µg/ml or less.

A preferred concentration of S-59 for pathogen inactivation in a platelet concentrate is approximately 50 µg/ml or less.

Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light (UVA). Further details of photoactive compounds that can be contained in the additive solution are described in U.S. Pat. No. 6,251,580, which is incorporated herein by reference.

The photoactivation device useful in activating the psoralens described above emits a given intensity of a spectrum of electromagnetic radiation comprising wavelengths between 180 nm and 400 nm, and in particular, between 320 nm and 380 nm. It is preferred that the intensity is less than 25 mW/sqcm (e.g. between 10 and 20 mW/sqcm) and that the mixture is exposed to this intensity for between one and twenty minutes (e.g. ten minutes).

The synthetic media 22, optionally mixed with plasma, can condition the platelet concentrate for other pathogen inactivating systems employing other types pathogen inactivating compounds. For example, other pathogen inactivating systems can employ other pathogen inactivating compounds such as phthalocyanine derivatives; phenothiazine derivatives (including methylene blue or dimethyl-methylene blue); endogenous and exogenous photosensitizers such as alloxazines, isoalloxazines (including riboflavin), vitamin Ks, vitamin L, napththoquinones, naphthalenes, naphthols, and other pathogen inactivating compounds disclosed in U.S. Pat. Nos. 6,258,577; 6,268,120; and 6,277,337, which are incorporated herein by reference; or "Pen 110", which is made by V.I. Technologies, Inc. (which is also known as the Inactine™ compound).

In one representative embodiment (e.g. for use with S-59), the synthetic media 22 comprises an aqueous solution of approximately: 45-120 mM sodium chloride; 5-15 mM sodium citrate; 20-40 mM sodium acetate; and 20-40 mM sodium phosphate. In a preferred embodiment, the aqueous solution comprises: approximately 70 to 90 mM sodium chloride; approximately 8 to 12 mM sodium citrate; approximately 25 to 35 mM sodium acetate; and approximately 22 to 35 mM sodium phosphate, which can be a combination of various protonated sodium phosphate species, e.g., dibasic sodium phosphate and monobasic sodium phosphate. The solution has a pH of approximately pH 7.0 to 7.4 and, preferably, approximately 7.2. By not containing glucose or magnesium, the media is readily autoclavable.

A preferred formulation for the solution 22 is prepared with the following ingredients:
Sodium Chloride: 77.3 mM
Sodium Acetate $3H_2O$: 32.5 mM
Sodium Citrate $2H_2O$: 10.8 mM
Monobasic Sodium Phosphate $1H_2O$: 6.7 mM
Dibasic Sodium Phosphate Anhydrous: 21.5 mM The solution can be formulated at about 99% of targeted concentrations to support shelf life, i.e., to account for water evaporation during storage. Furthermore, while the above formulation is the initial formulation, due to pH changes and/or adjustments, the ratio of acid to conjugate base of some of the ingredients may shift. This shift may alter the initial formulation during preparation and/or storage.

Using this formulation, it is desirable that the platelet additive solution 22 be combined with residual plasma in the platelet concentrate in a ratio of 50% to 80% by volume additive solution (with the remainder being plasma). A preferred ratio is 60% to 70% by volume additive solution (with the remainder being plasma). The most preferred ratio is about 65% additive solution by volume to about 35% plasma by volume. When other pathogen inactivating compounds and/or different synthetic media 22 are used, a different ratio by volume between the synthetic media 22 and plasma may exist, to optimize the effectiveness of the pathogen inactivating process.

The system 10 also preferably includes another solution container 16, which is integrally appended as part of the flexible transfer tubing array 20 to the primary container 12. The additive solution container 16 holds an additive solution 24 that is different than the platelet additive solution 22 in the container 18. The other additive solution 24 is intended for mixing with a blood component that is not a platelet-suspension.

For example, the other additive solution can be specially formulated for mixing with red blood cells, to serve as a storage medium. One such solution is disclosed in Grode et al U.S. Pat. No. 4,267,269, which is sold by Baxter Healthcare Corporation under the brand name ADSOL® Solution. Other examples include SAGM solution or CPDA-1 solution. The additive solution can be selected to condition the red blood cells for pathogen inactivation. For example, additive solutions of the type known as Erythrosol (also known as E-Sol or a related solution E-Sol A), can be mixed with the red blood cells to condition them for pathogen inactivation. E-Sol comprises sodium citrate (25 mM); dibasic sodium phosphate (16.0 mM); monobasic sodium phosphate (4.4 mM); adenine (1.5 mM); mannitol (39.9 mM); and dextrose (45.4 mM). E-Sol may be added to red blood cells as two separate components E-Sol A and a dextrose solution. E-Sol A comprises sodium citrate (26.6 mM); dibasic sodium phosphate (17.0 mM); monobasic sodium phosphate (4.7 mM); adenine (1.6 mM); and mannitol (42.5 mM). The pH's of E-Sol and E-Sol A range from 7.0 to 7.5, and preferably between 7.3 to 7.5. The above compositions can be made by modifying the stated concentrations by ±15%.

Desirably, the additive solution container 16, once emptied of the solution 24, is capable of storing another blood component, which is not the platelet-suspension nor the blood component mixed with the other additive solution 24.

In the system 10, the solution container 16 can receive a platelet-poor plasma component, which is the byproduct of the centrifugation of platelet-rich plasma to yield the platelet concentrate.

While not expressly shown, it is to be understood that the system 10 shown in FIG. 1 includes conventional external clamps and in-line frangible cannulas, which are manipulated in conventional fashion to control fluid flow within the system 10, as is well understood by persons of skill in the art of blood processing. The flexible tubing array 20 also includes conventional in-line Y-branch or T-branch connectors for the transfer tubing.

The containers and transfer tubing associated with each system illustrated in FIG. 1 can be made from any conventional approved, flexible, medical grade plastic materials, such as polyvinyl chloride plasticized with di-2-ethylhexyl-phthalate (PVC-DEHP). Such containers are formed using conventional heat sealing technologies, e.g., radio frequency (RF) heat sealing. However, the transfer container 14 that is intended to serve as the storage container for the platelet-suspension is desirably made of blow molded polyolefin material (as disclosed in Gajewski et al U.S. Pat. No. 4,140,162) or a heat sealed polyvinyl chloride material plasticized with tri-2-ethylhexyl trimellitate (TEHTM), or a blend of styrene ethylene butylene styrene (SEBS) block copolymer (e.g., KRATON® G-1652M), ethylene vinyl acetate (EVA), and ultra-low density polyethylene (UL-DPE), which is manufactured by Baxter Healthcare Corporation under the designation PL-2410). These materials, when compared to DEHP-plasticized polyvinyl chloride materials, have greater gas permeability that is beneficial for platelet storage.

As described, the system 10 serves at least two processing objectives. The first objective is to process, in an integral, sterile, closed system, a unit of whole blood to obtain a red blood cell component (RBC), a platelet concentrate component (PC), and a platelet poor plasma component (PPP). A second objective is to condition, in an integral, sterile, closed system, the PC component for pathogen inactivation, as well as further processing, e.g., long term storage, and/or pooling, or combinations thereof.

In this arrangement, the platelet additive solution 22 in the container 18 also serves as a resuspension solution for the PC component in the storage container 14. This frees up more PPP for collection. The system 10 thereby also maximizes recovery of PPP.

In use, once the primary container 12 receives whole blood from a donor, the donor tubing 26 and phlebotomy needle 28 are disconnected from the rest of the system 10. The separation of the donor tubing 22 can be accomplished by forming a snap-apart seal in the donor tubing 26 using a conventional heat sealing device (for example, the Hematron® dielectric sealer sold by Baxter Healthcare Corporation). The whole blood is mixed with the anticoagulant.

Whole blood is then separated by centrifugation in the primary container 12 into red blood cells (RBC component) and platelet-rich plasma (PRP component). The heavier RBC component collects in the bottom of the primary container 12 during processing. The lighter PRP plasma component collects at the top of the primary container 12 during centrifugation. During centrifugal separation, an intermediate layer of leukocytes typically forms between the RBC component and the PRP component.

Following centrifugal separation, the PRP component is expressed from the primary container 12 through the tubing array 20 into the transfer container 14. A conventional V-shaped plasma press can be used for this purpose. The expression is desirably monitored to keep as much of the intermediate layer, and the leukocytes contained therein, with the RBC component in the primary container 12.

The solution 24 held by the additive solution container 16 can be transferred into the RBC component in the primary container 12. The first additive solution is then mixed with the RBC component.

The primary container 12 can be detached from the rest of the assembly by forming a snap-apart seal formed by a conventional dielectric sealing device, as previously described. Of course, the RBC component may then undergo further processing, e.g., leukocyte filtration (as will be discussed in detail later) and/or pathogen inactivation.

Next, the PRP component is centrifugally separated in the container 14 to separate a majority of the platelets out of the plasma, thereby creating the PC component and the PPP component.

The PPP component can be expressed from the transfer container 14 through tubing array 20 into the (now emptied) first additive solution container 16. A conventional V-shaped plasma press can be used for this purpose, as previously described. A desired residual volume of the PPP component is left with the PC component in the transfer container 14. The first additive solution container 16, containing the PPP component volume expressed from the container 14, can be detached from the rest of the system 10 by forming a snap-apart seal using a conventional dielectric sealing device, as previously described. Like the RBC component, the PPP component can then undergo further processing, e.g., cellular filtration, and/or pathogen inactivation, and/or freezing to form fresh frozen plasma for storage and/or fractionation.

The platelet additive solution 22 can be transferred from the additive container 18 through the tubing array 20 into the transfer container 14. The platelet additive solution 22 is mixed with the PC component and plasma volume in the desired proportion, as already discussed. The additive container 18 can be detached from the remaining assembly by forming a snap-apart seal formed by a conventional dielectric sealing device, as previously described.

Like the RBC and PPP components, the PC component, mixed with plasma and the additive solution 22, can then undergo further processing, e.g., leukocyte filtration, and/or pathogen inactivation, and/or storage, and/or pooling, or combinations thereof. For example, as shown in FIG. 2A, a desired number of the containers 14, each containing a unit of the PC component premixed with plasma and the platelet additive solution 22, can be coupled to a pooling kit 44. The pooling kit 44 makes possible the combination of random donor units of platelets into a therapeutic dose of platelets prescribed for transfusion.

The pooling kit 44 includes a pooling container 40 coupled to an array of multiple tubing leads 42. Six tubing leads 42 are shown in FIG. 2A, which enable the pooling in the container 40 of six, random donor units of the PC component premixed mixed with plasma and the platelet additive solution 22. This is because, typically, a therapeutic dose of platelets comprises six manual donor units. Fewer or greater number of leads 42 can, of course, be provided, depending upon the circumstances.

A given container 14 can be individually coupled to a given one of the leads 42 in various ways. For example (as FIG. 2A shows), a closed tubing segment or appendage 140 on the container 14 can be coupled to the lead by a sterile docking technique, such as disclosed in Spencer U.S. Pat. No. 4,412,835 or Granzow et al U.S. Pat. Nos. 4,157,723 and 4,265,280, which are incorporated herein by reference.

In this arrangement, the attachment is made without otherwise opening communication with the atmosphere. The result is an essentially sterile connection. As a result, the PC components can be stored in the pooling container 40 for the maximum allowable dating period.

Alternately, a non-sterile connection, e.g., insertion of a conventional blood spike into a port of a container 18, can be utilized (not shown). This attachment technique, however, opens the communication with the atmosphere. As a result, the pooled PC components must be transfused quickly in accordance with local governmental regulations. On the other hand, agencies regulating blood collection and/or processing activities may someday permit the storage of pooled PC components collected in open systems for longer periods of time, if the pooled PC components are pathogen inactivated. In this circumstance, the pooling kits described need not necessarily comprise closed blood processing systems.

As shown in FIG. 2B, instead of being coupled in parallel via the leads 42 to the pooling container 40 (as FIG. 2A shows), the containers 14 can alternatively be coupled in series to the pooling container 40, in an arrangement also called "the train." In this embodiment, each container 14 includes top and bottom closed tubing segments or appendages 140. A bottom segment 140 of an upper container 14 is coupled to a top segment 140 on the next adjacent lower container 14, and so on, preferably using a sterile docking technique, as already described, to the form the train. The PC components premixed with plasma and the additive solution 22 are drained into the pooling container 40 through the chain of interconnect containers 14 forming the train.

Regardless of whether the containers 14 are drained in parallel (FIG. 2A) or in series (FIG. 2B), the pooling kit 44 may also include an appropriate in-line leukocyte-reduction filter 43, which is desirably located adjacent the inlet of the pooling container 40. This arrangement accomplishes leukocyte-filtration of the PC component premixed with plasma and the platelet additive solution 22 in the process of pooling multiple random donor units. In this arrangement, a bypass branch 46 desirably extends around the leukocyte-reduction filter 43. The bypass branch 46 allows for the expression of air from the pooling container 40. This also allows for more complete drainage to maximize post-pooling and filtration platelet recovery. A one-wave valve V is also desirably provided in the bypass branch 46 to permit fluid flow only in the direction toward the containers 14, preventing fluid flow in the opposite direction.

Since each individual PC component unit (i.e., the PC component collected and processed in the container 14) already contains plasma and the platelet additive solution 22, the pooled units in the container 40 are conditioned for pathogen inactivation. The platelet additive solution 22 has been mixed with the PC components in a closed integral system, and thereby eliminates the need to later provide a sterile connection for each PC component to receive an additive solution 22, e.g., during subsequent pooling.

Alternatively, if desired, each individual unit (in the container 14) can separately undergo pathogen inactivation prior to or instead of being pooled.

Thus, the system 10 provides manually-processed individual random donor PC component units, which can undergo pathogen inactivation in a manner that is both time-efficient and cost-efficient. The system 10 diminishes reliance on automated methods to provide PC components suitable for pathogen inactivation.

As shown in FIG. 2A, the pooling kit 44 can optionally include a storage container 48 coupled to the pooling container 40 via a transfer tubing branch 50. The presence of the storage container 48 allows the pooled platelet PC components to undergo further centrifugal processing in the pooling container 40 to provide for a secondary removal of red blood cells, which can lead to a more pure platelet product suspended in platelet additive solution. After centrifugation, the pooled platelet components, in the presence of the additive solution 22, can be express (using, e.g., a V-shape press) from the pooling container 40 into the storage container 48, taking care (e.g., through visual monitoring or electrical interface detection techniques) to retain the separated residual red blood cells in the pooling container 40. Thus, a pooled platelet component conditioned for pathogen inactivation can be provided that is also essentially free of the presence of red blood cells. Residual red blood cells can be further isolated from the pooled platelet components in the pooling container 40 in other ways, as will be described in greater detail later.

In an optional arrangement (shown in phantom lines in FIGS. 2A/2B), the transfer tubing branch 50 can further include an appropriate in-line leukocyte-reduction filter 52, with appropriate air venting bypass branch 54 and one-way valve V. The filter 52 can be used in combination with the filter 43, to achieve a secondary removal of leukocytes from the pooled platelet components. The filter 52 can be used in the place of the filter 43, for leukocyte-reduction in the first instance.

Figure 4:
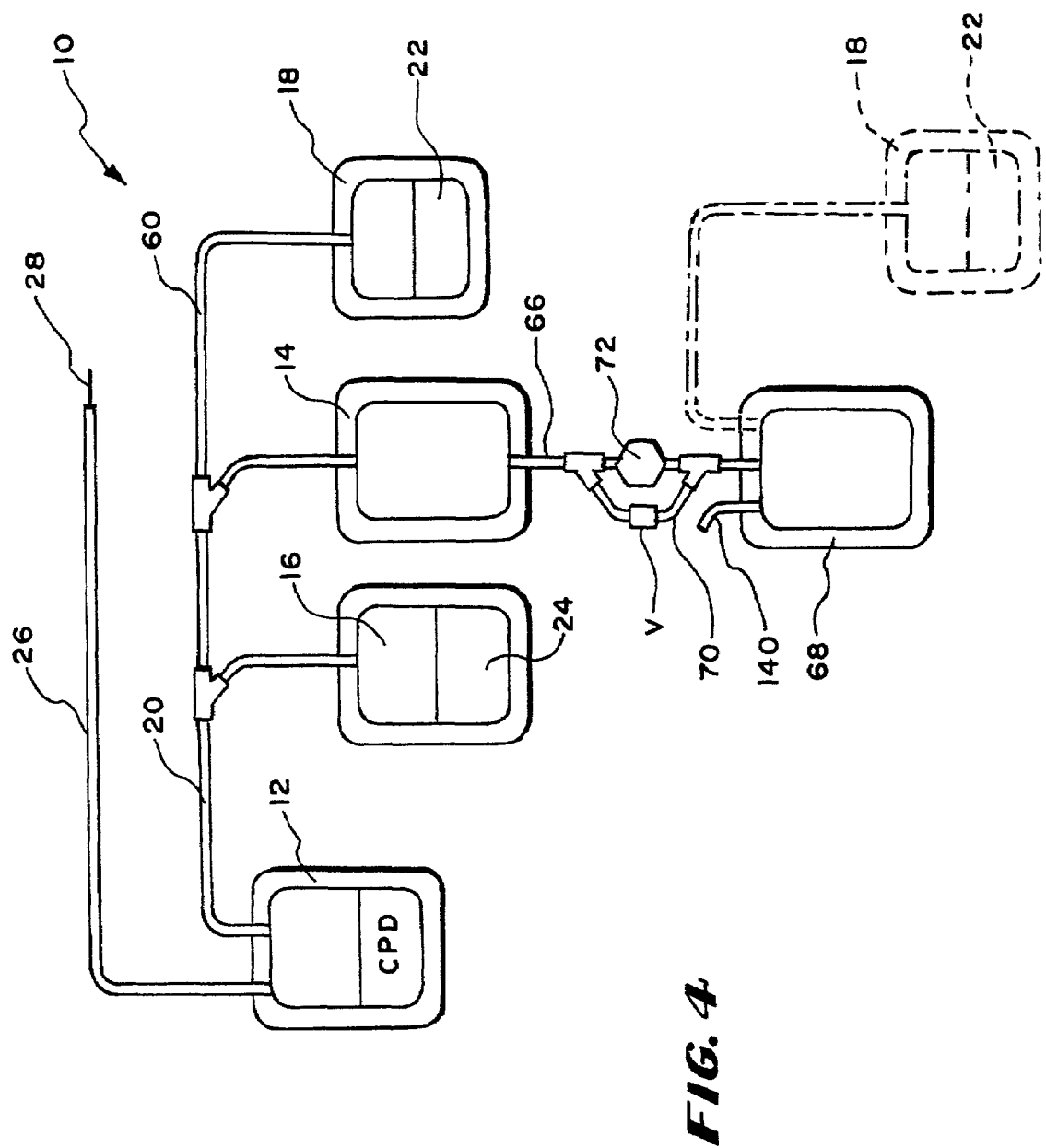
FIG. 4 is an alternative embodiment of a blood processing system accommodating the mixing of a platelet additive solution to a platelet component within an integral, sterile closed system, as well as accommodating the filtering of the mixture to remove leukocytes, to thereby condition the platelet component for pathogen inactivation in a leukocyte-reduced state.

A leukocyte-reduced platelet component unit, premixed in a closed integral system with plasma and an additive solution 22, can be processed prior to pooling. As shown in FIGS. 3 and 4, the system 10 can itself make possible leukocyte-filtration of an individual unit of PC component prior to pooling, either before or after mixing with the platelet additive solution 22. In this arrangement, a multiple lead kit 40 (such as shown in FIG. 2A) provided to pool individual units of PC components, need not include a leukocyte-reduction filter or counterpart leukocyte removal function.

As one example, shown in FIG. 3, the tubing branch 60 between the transfer container 14 and the additive solution container 18 can include an appropriate in-line leukocyte-reduction filter 64. A bypass branch 62 extends around the leukocyte-reduction filter 64.

A one-wave valve V may also be provided in the bypass branch 62 to permit fluid flow only in the direction toward the container 14, preventing fluid flow in the opposite direction.

In use, after transfer of the PPP component from the container 14, the platelet additive solution 22 can be conveyed through the bypass branch 62 from the container 18 into the container 14 for mixing with the plasma and PC component. After mixing, the PC component, plasma, and additive solution 22 can be conveyed through the leukocyte-reduction filter 64 into the container 18. Residual air can be vented from the container 18 through the bypass branch 62 into the container 14. In this arrangement, the additive solution container 18 ultimately serves as the storage container for the leukocyte-reduced PC component, after mixing with plasma and the platelet additive solution 22.

Of course, the PC component and plasma can be conveyed from the container 14 directly through the filter 64, without a prior transfer of additive solution 22 for mixing with the PC component. In this arrangement, the PC component and plasma mix with the additive solution upon entering the container 18. Still, it is desirable to mix the platelet additive solution 22 prior to passage of the PC component and plasma through the leukocyte-reduction filter 64. The premixing of the PC component with the additive solution 22 eliminates the need to manually agitate a PC component, plasma, and additive solution mixture after leukocyte filtration. Mixing also lowers the viscosity of the PC component, leading to overall higher flow rates during leukocyte filtration, as well as mediates damage or activation of the platelets during processing.

As another example, as shown in FIG. 4, a transfer tubing branch 66 can be provided between the transfer container 14 and an additional transfer container 68. The additional tubing branch 66 can include an appropriate in-line leukocyte-reduction filter 72. A bypass branch 70 desirably extends around the leukocyte-reduction filter 72. A one-wave valve V also may be provided in the bypass branch 70 to permit fluid flow only in the direction toward the container 14, preventing fluid flow in the opposite direction.

In use, after transfer of the PPP component from the container 14 into the container 16, the platelet additive solution 22 can be conveyed into the container 14 for mixing with the PC component and remaining plasma, as previously explained. After mixing, the PC component, plasma, and additive solution 22 can be conveyed via the transfer tubing branch 60 through the leukocyte-reduction filter 72 into the transfer container 68. Residual air can be vented from the container 68 through the bypass branch 70 into the container 14. In this arrangement, the container 68 ultimately serves as the storage container for the leukocyte-reduced PC component, mixed with plasma and the platelet additive solution 22.

Alternatively, as shown in phantom lines in FIG. 4, instead of the being coupled to the container 14 by tubing 60, the additive solution container 18 can be directly coupled to the transfer container 68 to transfer the additive solution 22 into the container 68 either before, after, or during passage of the PC component and plasma through the filter 72. Still alternatively, the platelet additive solution 22 can be stored in the container 68 for mixing with the PC component and plasma while leukocyte filtration occurs. Still, as discussed above, it is desirable to mix the additive solution 22 with the PC component and plasma prior to leukocyte filtration.

Figure 5:
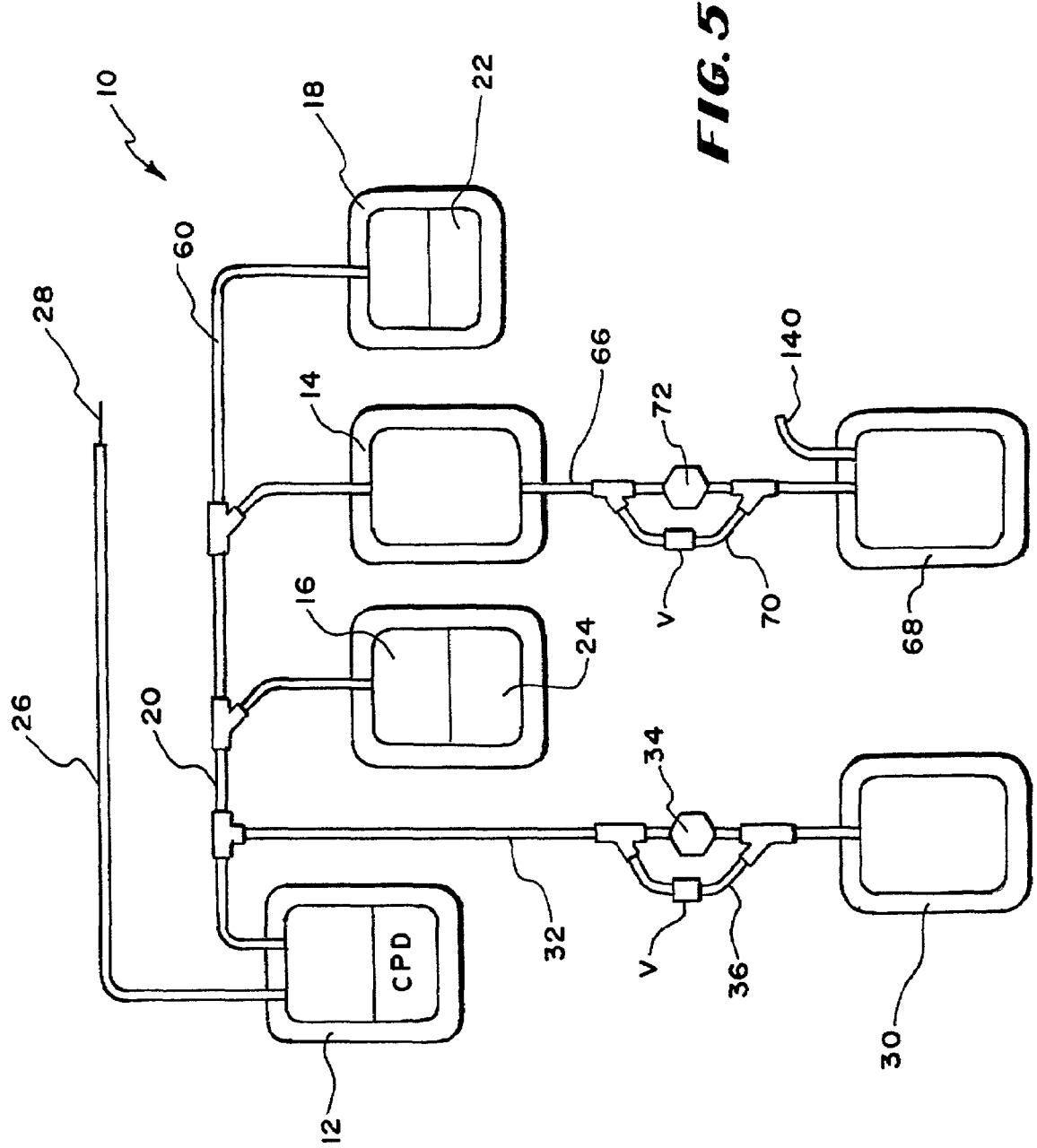
FIG. 5 is a blood processing system like FIG. 4, which accommodates the mixing of a platelet additive solution to a platelet component within an integral, sterile closed system, as well as the filtering of the mixture to remove leukocytes, to thereby condition the platelet component for pathogen inactivation in a leukocyte-reduced state, and which further accommodates the filtering of a red blood cell component (mixed with an additive solution) to remove leukocytes.

In another alternative embodiment (see FIG. 5), the system 10 can also provide an in-line leukocyte-reduction function for the other cellular blood component, i.e., the red blood cells. In this arrangement, the system 10 includes a second transfer container 30 coupled by a flexible transfer tubing branch 32 and the flexible tubing array 20 to the primary container 12. The transfer tubing branch 32 carries an in-line leukocyte-reduction filter 34. A bypass branch 36 with one way valve V are also desirably provided for air venting. Blood samples may also be collected in the bypass branch 36. A one-wave valve (not shown) may be provided in the bypass branch 36 to permit fluid flow only in the direction toward the container 12, preventing fluid flow in the opposite direction. The filter 34 for the red blood cell component can be used in the system 10 in association with the filter 72 for the platelet component as FIG. 5 shows, or the filter 64 for the platelet component shown in FIG. 3. Alternatively, the filter 34 for the red blood cell component can be used in the system 10 in the absence of the filter 72/64 for the platelet component.

The manipulation of the system 10 shown in FIG. 5 is generally the same as manipulation of the system 10 shown in FIG. 1. The exception is that, following transfer of the additive solution 24 into the RBC component in the primary container 12, the RBC component, mixed with the additive solution 24, is conveyed through the transfer tubing branch 32 into the container 30 through the filter 34. Residual air in the container 30 is vented through the bypass branch 36 into the primary container 12. The container 30 serves as the storage container for the leukocyte-reduced RBC. The pre-mixing of the red blood cell component with the additive solution 24 eliminates the need to manually agitate a red blood cell-additive solution mixture after leukofiltration. The mixing also lowers the viscosity of the red blood cells and leads to higher flow rates during leukofiltration without hemolysis during processing. Nevertheless, it should be appreciated that it may be desirable for other reasons to mix the red blood cell additive solution 24 with the red blood cells after leukofiltration. In this arrangement, a container holding the additive solution 24 can be directly integrally coupled to the second transfer container 30.

The foregoing has described the manipulation of a random donor PC component that is formed at the outset from the separation of a platelet concentrate from a platelet-rich plasma. However, it should be appreciated that the whole blood may be centrifugally separated in the primary container 12 at higher centrifugation speeds (also called a "hard spin"). The hard spin forces a large number of platelets out of the plasma and into the intermediate buffy coat layer, which forms between the plasma component and the red blood cell component during centrifugation. In this arrangement, the PC component comprises a random donor, platelet-rich buffy coat unit. The additive solution 22 can be added to condition the platelets in the random donor, platelet-rich buffy coat for pathogen inactivation within a closed, sterile blood processing system in essentially the same manner as just described and with the same beneficial results. The conditioned platelets can be subsequently harvested for pathogen inactivation from the buffy coat by subjecting a desired number of conditioned pooled random donor buffy coat units to centrifugation. The centrifugation separates residual red blood cells and white blood cells from the platelets prior to pathogen inactivation. It should also be appreciated that the number and arrangement of containers in a given blood processing system can vary according to the blood processing objectives.

Figure 6:
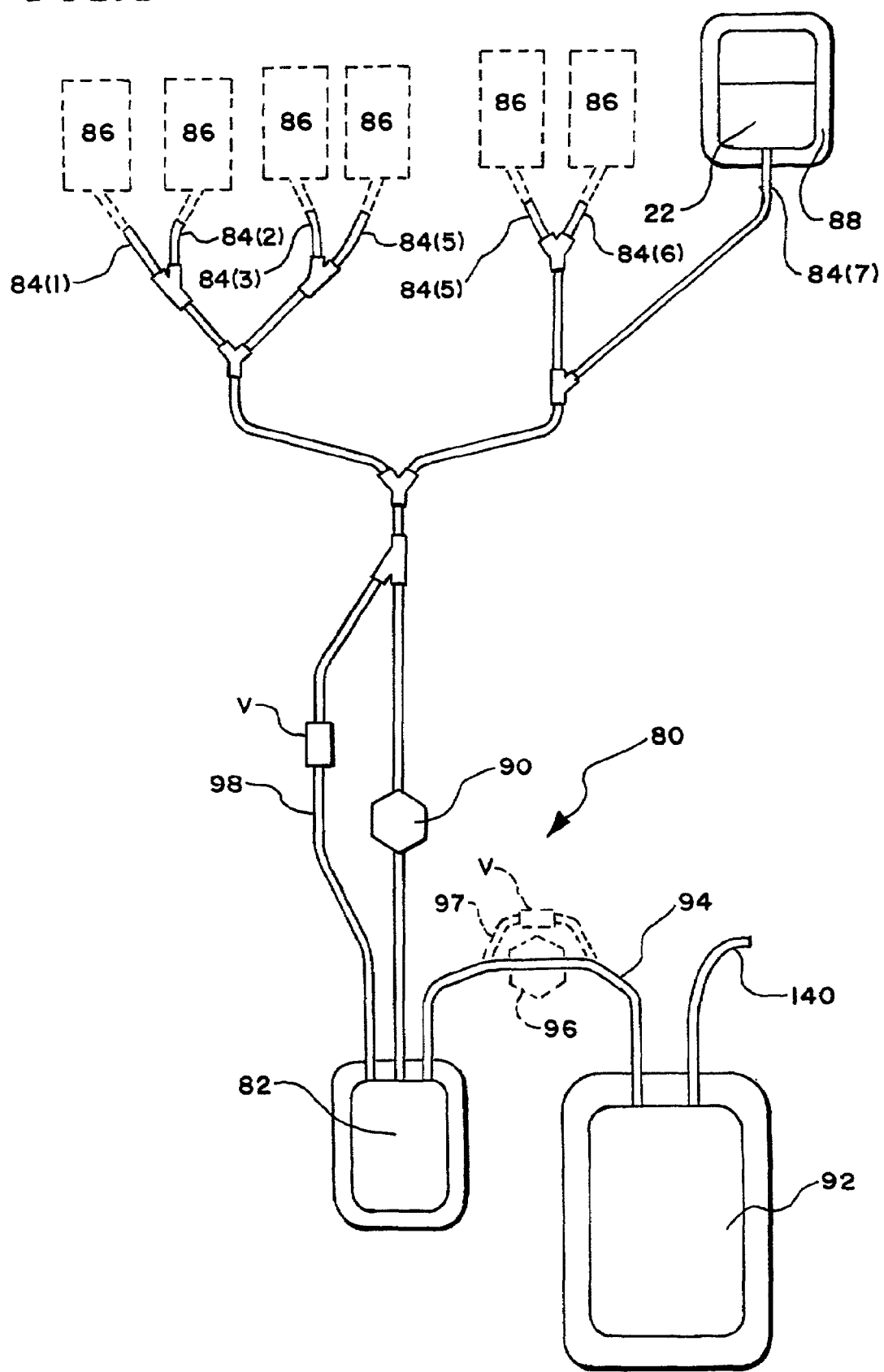
FIG. 6 is a kit for pooling random donor units of platelet components while mixing a platelet additive solution with the pooled units, to thereby condition the pooled units for pathogen inactivation.

FIG. 6 shows an alternative embodiment of a pooling kit 80 for PC components that are not mixed with a platelet additive solution 22 during initial processing. In this arrangement, the pooling kit 80 includes a pooling container 82 coupled to an array of multiple tubing leads 84. Seven tubing leads 84(1) to 84(6) are shown in FIG. 6. Six of the leads 84(1) to 84(6) enable the pooling in the container 82 of six containers 86, each containing one random donor unit of the PC component (and a desired volume of plasma) not mixed with platelet additive solution 22. The seventh lead 84(7) enables the addition of a platelet additive solution 22 from a container 88 while pooling occurs. As before explained each container 86 and 88 can be coupled to one of the leads 84 using either sterile or non-sterile docking techniques. Alternatively, the container 88 holding the additive solution 22 can be integrally coupled to the kit 80 during manufacture.

Of course, as explained above, the pooling kit 80 may contain a fewer or greater number of leads than seven, depending upon the starting amounts of random donor platelet units and the desired therapeutic dose. An interconnected chain of containers 86 forming a train (in place of the containers 14, as shown in FIG. 2B) may also be used to convey the PC component mixed with plasma into the pooling container 82. In this arrangement, as shown in phantom lines in FIG. 2B, the platelet additive solution 22 (in container 88) is desirably coupled to the pooling container 82, for mixing the solution 22 with the train-pooled PC components.

As shown in FIG. 6, the pooling kit 80 may include an appropriate in-line leukocyte-reduction filter 90, which is desirably located between the junction of all the leads 84 and the pooling container 82. A bypass branch 98 with a one way valve V is also desirably provided in this arrangement for air venting purposes, as already described. This arrangement accomplishes the leukocyte-filtration of the PC component, while mixing with the platelet additive solution 22 occurs, all in the process of pooling multiple random donor units.

Optionally, as also shown in FIG. 6, the pooling kit 80 can include a storage container 92 coupled to the pooling container 82 via a transfer tubing branch 94. The transfer tubing branch 94 can include an appropriate in-line leukocyte-reduction filter 96 (with bypass branch 97 and one way valve V) (as shown in phantom lines in FIG. 6), either in addition to the filter 90 or instead of the filter 90. As explained in the context of the pooling kit 40 shown in FIGS. 2A/2B, this arrangement would be useful if there is a desire to separate residual red blood cells from the PC components in the pooling container 82 after pooling, e.g., by centrifugation or gravity sedimentation. The platelet component can then be transferred from the pooling container 82 into the container 92 (using, e.g., a V-shaped press), taking care (e.g., through visual monitoring or electrical interface detection techniques) to retain the residual red blood cells in the pooling container 82. Thus, a pooled platelet component conditioned for pathogen inactivation can be provided that is also essentially free of the presence of red blood cells.

In either pooling kits 44 or 80 shown in FIG. 2A and FIG. 6, respectively, other means can be provided to keep residual red blood cells separated from pooled platelet components in the pooling container isolated from the platelet component, to provide a pooled platelet component that is both conditioned for pathogen inactivation and essentially free of the presence of red blood cells.

For example, as shown in FIG. 7, a pooling kit 80A of the type shown in FIG. 6 (which can also comprise a pooling kit of the type shown in FIGS. 2A/2B) includes a pooling container 120 having a bottom region that is tapered to present a reduced volume red blood cell collection region 122. As shown in FIG. 7, the shape and size of the region 122 is defined by heat seals formed in the walls of the container 120. Alternatively (not shown), a preformed molded or extruded structure can be heat sealed to the bottom of the container 120, to form the reduced volume, red blood cell collection region 122.

Red blood cells can be allowed to sediment by gravity into the reduced volume region 122 of the pooling container 120. The presence of the platelet additive solution 22 may enhance the gravity sedimentation process. Alternatively, the pooling container 120 can undergo centrifugation with the region 122 oriented in the high-G field, so that residual red blood cells centrifugally separated from the platelet component will collect in response to centrifugal forces in the reduced volume region 122.

When centrifugal separation is used, the pooling container 120 is desirably placed into a centrifugation cup that is sized and shaped to hold and support the reduced volume region 122 in the high-G field. The centrifuge cup can be constructed and configured in various ways.

Figure 16:
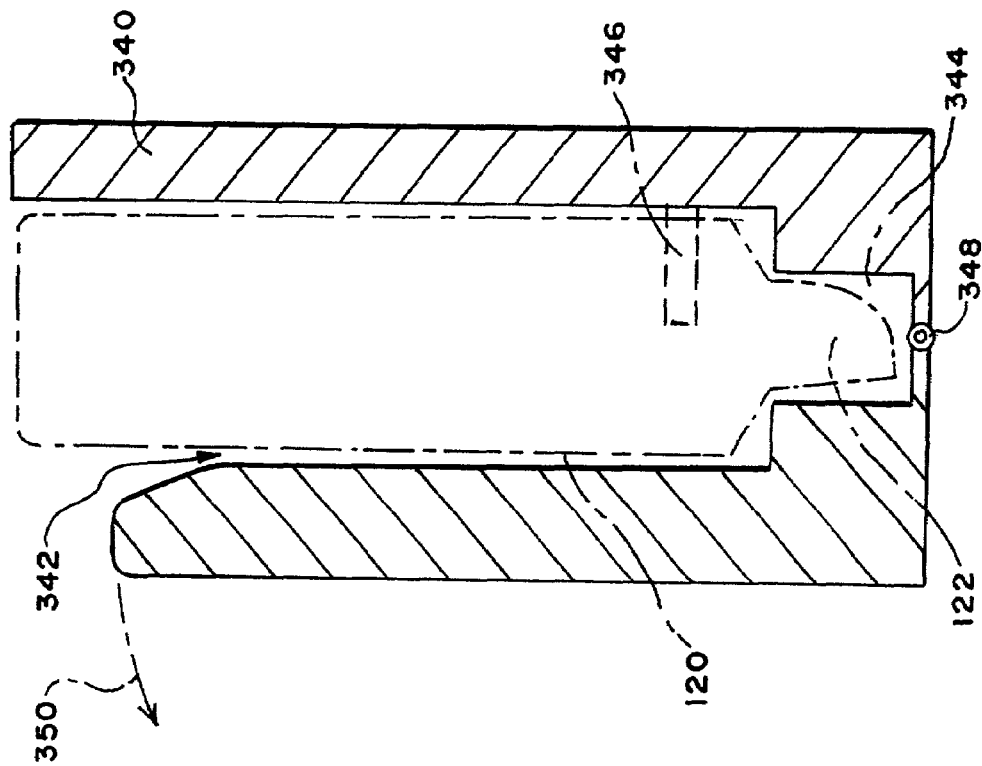
FIG. 16 is a side section view of a centrifuge cup that can be used to hold a pooling container of a type shown in FIG. 7 during centrifugation to separate residual red blood cells from a pooled platelet component.

In a representative embodiment shown in FIG. 16, a centrifuge cup 340 includes an interior chamber 342. The interior chamber 342 receives the pooling container 122 (shown in phantom lines in FIG. 16) for rotation on the centrifuge rotor (not shown). The cup 340 can include a hinge 348, to swing open the interior chamber 342 in the manner of a clam shell (as indicated by arrow 350) to facilitate loading the container 120.

As FIG. 16 also shows, the bottom of the interior chamber 342 (which, during rotation of the centrifuge rotor, is oriented in the high-G field) includes a pocket 344. The pocket 334 is sized and shaped to receive the reduced volume region 122 (shown in phantom lines in FIG. 16) of the container 120. During centrifugation, the reduced volume region 122 is held in the pocket 334 in the high-G field for collection of residual red blood cells. One or more locator pins 336 may be provided in the chamber 332, to mate with locator holes 338 formed on the pooling container 120 (see FIG. 7), to further stabilize and support the reduced volume region 122 in the chamber pocket 334.

Once centrifugation (or gravity sedimentation) is complete, a clamping device 124 or the like (as shown in phantom lines in FIG. 7) seals the region 122 from the remainder of the container 120. As FIG. 7 shows, the region 122 desirably forms an appendage not attached along its sides to the container 120, to facilitate positioning of the clamping device 124 and to minimize the extent of the required clamping area. The clamping device 124 forms a seal across the region 122 that mechanically isolates the residual red blood cells in the pooling container 120 from the PC component. The pooling container 120 may be subsequently handled with the clamping device 124 in place. Alternatively, the seal across the region 122 can be formed by radio frequency sealing, obviating the need for an external clamping device 124. Optionally, as shown in phantom lines in FIG. 7, the platelet component (essentially free of red blood cells) can be expressed into a connected storage container 92 (e.g., by use of a V-shaped press). Due to the clamping device 124, manual or electrically aided interface detection techniques are obviated.

As another example, as shown in FIG. 8, a pooling kit 80B of the type shown in FIG. 6 (which can also comprise a pooling kit of the type shown in FIGS. 2A/2B) includes a pooling container 126 having a top region 128 that is tapered. During centrifugation of the pooling container 126, the region 128 is oriented in the low-G field, so that residual red blood cells centrifugally separated (or sedimented by gravity) from the platelet component will collect in the lower (high-G) region of the container 126. Once centrifugation or sedimentation is complete, expression of the pooled platelet component proceeds through the tapered upper region 128 into the storage container 92. The reduce volume upper region 128 concentrates the interface of separated red blood cells into a smaller area. This makes it easier to visually or electrically detect the interface and control the transfer of components essentially free of red blood cells into the storage container 92.

As yet another example, as shown in FIG. 9, a pooling kit 80B of the type shown in FIG. 6 (which can also comprise a pooling kit of the type shown in FIG. 2A or 2B) includes a pooling container 130 having a bottom region that is gradually tapered to present a red blood cell collection region 132. A small volume red blood cell isolation container 134 is coupled to the red blood cell collection region 132 through a tubing branch 136, which also carries an in-line one-way valve 138. The one-way valve 138 permits fluid flow from the collection region 132 toward the isolation container 134, but not in the opposite direction. During centrifugation of the pooling container 130, the region 132 is oriented in the high-G field, so that residual red blood cells centrifugally separated from the platelet component will collect in the region 132. As before explained, gravity sedimentation can also be used. Once centrifugation (or sedimentation) is complete, the residual red blood cells in the region 132 are expressed through the one-way valve 138 and tubing branch 136 into the isolation container 134. Once the desired residual volume of blood is drained into the isolation container 134, the tubing branch 136 is sealed and separated (e.g., by forming a snap-apart seal using a conventional heat sealing device). This arrangement eliminates the need for an addition container 92, as pooled platelet components are both conditioned for pathogen inactivation and are essentially free of red blood cells in the pooling container 130.

In the illustrated embodiment, filtration serves to remove leukocytes from blood components. It should be appreciated, however, that leukocyte separation can occur by various centrifugal and non-centrifugal techniques, and not merely "filtration" in the technical sense. Separation can occur by absorption, columns, chemical, electrical, and electromagnetic means. "Filtration" is broadly used in this specification and encompasses all of these separation techniques as well.

The leukocyte filters described above can be variously constructed. In the embodiment illustrated in FIGS. 10A and 10B, the filter F comprises a housing 100 inclosing a filtration medium 102 that can comprise either a membrane or a fibrous material. The filtration medium 102 can be arranged in a single layer or in a multiple layer stack. If fibrous, the medium 102 can include melt blown or spun bonded synthetic fibers (e.g., nylon or polyester or polypropylene), semi-synthetic fibers, regenerated fibers, or inorganic fibers. If fibrous, the medium 102 removes leukocytes by depth filtration. If a membrane, the medium 102 removes leukocytes by exclusion.

The housing 100 can comprise rigid plastic plates sealed about their peripheries. In the illustrated embodiment, the housing 100 comprises first and second flexible sheets 104 of medical grade plastic material, such as polyvinyl chloride plasticized with di-2-ethylhexyl-phthalate (PVC-DEHP). Other medical grade plastic materials can be used that are not PVC and/or are DEHP-free.

In the illustrated embodiment, a unitary, continuous peripheral seal 106 (see FIG. 10B) is formed by the application of pressure and radio frequency heating in a single process to the two sheets 104 and filtration medium 102. The seal 106 joins the two sheets 104 to each other, as well as joins the filtration medium 102 to the two sheets 104. The seal 106 integrates the material of the filtration medium 102 and the material of the plastic sheets 104, for a reliable, robust, leak-proof boundary. Since the seal 106 is unitary and continuous, the possibility of blood shunting around the periphery of the filtration medium 102 is eliminated.

The filter F also includes inlet and outlet ports 108. The ports 108 can comprise tubes made of medical grade plastic material, like PVC-DEHP. In the embodiment shown in FIGS. 10A and 10B, the ports 108 comprise separately molded parts that are heat sealed by radio frequency energy over a hole 109 formed in the sheets 104 (see FIG. 10A).

The systems and methods described above make possible the handling of platelet components, which have been manually collected in sterile closed systems as random donor platelet units, in pathogen inactivation processes designed to meet the demand for larger, therapeutic doses of platelet components. Typically, online, automated blood processing systems and methods are used to meet the demand for these larger therapeutic doses of pathogen inactivated platelet components. The systems and methods described above make possible new systems and methods that merge the manual collection of random donor platelet units with the creation of larger therapeutic doses of platelets targeted to undergo pathogen inactivation prior to long term storage and/or transfusion.

Figure 11:
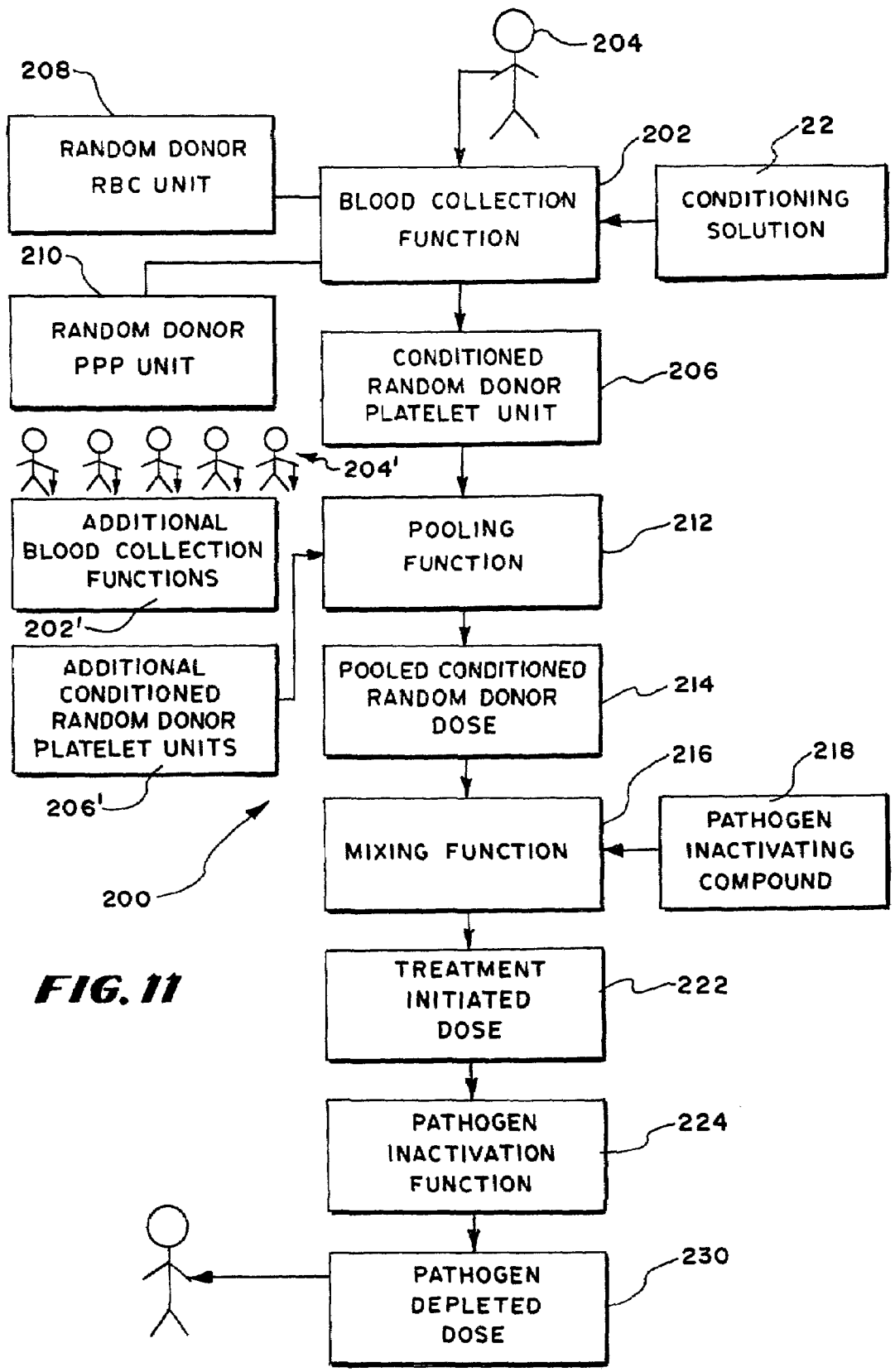
FIG. 11 is a schematic view of a blood processing system and related method that provide platelet components harvested in sterile closed systems as random donor units, which are conditioned for pathogen inactivation either individually or in pooled units.

For example, as shown in FIG. 11, a system and related method 200 can include a manual blood collection function 202. The function 202 processes blood drawn from an individual donor 204. The function 202 can comprise the closed, sterile, manually manipulated blood collection and storage systems 10 shown in FIG. 1 or 3 or 4 or 5.

The function 202 generates a random donor sterile platelet component unit 206. Unlike other random donor platelet units, the unit 206 generated by the function 202 has been conditioned for pathogen inactivation by the mixing, in a sterile, closed system, of plasma and a prescribed platelet additive solution 22. The random donor sterile platelet component unit 206 is also suited for long term storage in the absence of pathogen inactivation. The function 202 can also have subjected the random donor sterile platelet component unit 206 to closed system leukocyte filtration, so that the unit 206 is conditioned for pathogen inactivation and/or long term storage in a leukocyte-reduced state.

The function 202 can also generate a random donor sterile red blood cell (RBC) unit 208 (which can also have undergone closed system leukocyte filtration) and/or a random donor sterile platelet poor plasma (PPP) component unit 210, either or both of which are suited for long term storage and/or pathogen inactivation, as will be described later in greater detail.

The system and method 200 also includes a pooling function 212. The pooling function 212 receives a plurality of random donor sterile platelet component units 206, which have been conditioned by the previous function 202 for pathogen inactivation. One unit 206 is received from the function 202 associated with the donor 204, and the remaining units 206' are received from counterpart functions 202' associated with other random donors 204'. The pooling function 212 can comprise the closed, sterile, manually manipulated pooling kits shown in FIG. 2 or 7 or 8 or 9.

The function 212 generates a pooled random donor sterile platelet component dose 214. The dose 214 is conditioned for pathogen inactivation, because each random donor sterile platelet component unit 206 contained plasma and a premixed platelet additive solution 22. The pooled random donor sterile platelet component dose 214 is suited for long term storage in the absence of pathogen inactivation. The function 212 can also have subjected the pooled random donor sterile platelet component dose 214 to closed system leukocyte filtration, so that the dose 214 is conditioned for pathogen inactivation and/or long term storage in a leukocyte reduced state. The function 212 can also have subjected the pooled random donor sterile platelet component dose 214 to closed system centrifugation, so that the dose 214 is essentially free of red blood cells and is conditioned for pathogen inactivation and/or long term storage in this red blood cell-free state.

Figure 12:
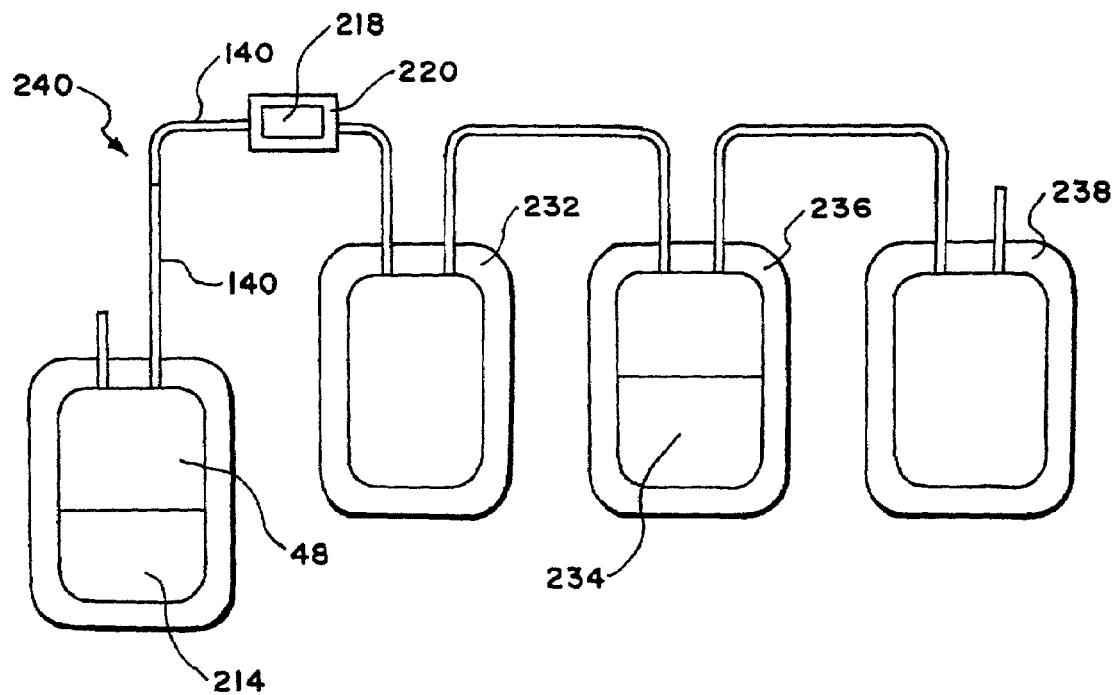
FIG. 12 is a system that performs the function incorporated in the system and method shown in FIG. 11, of sterile mixing a pooled dose of platelet components, preconditioned for pathogen inactivation, with a pathogen inactivating compound, to form a treatment-ready pooled dose.

The system and method 200 also includes a pathogen inactivating compound mixing function 216. The mixing function 216 receives a pooled random donor sterile platelet component dose 214 and mixes with it a desired volume of a pathogen inactivating compound 218 (see FIG. 12). As FIG. 12 shows, this mixing is desirably accomplished in a sterile fashion, by coupling the closed tubing segment 140 on the pooling kit container 48 (as also shown in FIG. 2A) to counterpart closed tubing segment 140 carried by an in-line container 220 that contains the pathogen inactivating compound 218, using a suitable sterile docking technique (as already described). In the absence of the pooling kit container 48 (i.e., in the absence of residual red blood cell removal during the pooling function 212), the pooling kit container 40 itself could carry the tubing segment 140 for sterile docking. Mixing is completed by transferring the platelet component dose 214 from the pooling container 48 (or 40) through the in-line container 220 into a transfer container 220.

The mixing function 216 generates a treatment-initiated pooled random donor dose 222, which is contained after mixing in the transfer container 232. The treatment-initiated pooled random donor dose 222 comprises the pooled random donor sterile platelet component dose 214 mixed with the pathogen inactivating compound 218 (see FIG. 11).

In the absence of a pooling function 212, the pathogen inactivating compound 218 can be individually mixed with a random donor sterile platelet component unit 206 (generated by the function 202) by sterile docking with the tubing segment 140 carried by the transfer container 14 (see FIG. 1 or 3) or by the transfer container 68 (see FIG. 4 or 5). In this arrangement, the random donor sterile platelet component unit 206 could undergo pathogen inactivation during the next function 224.

The system and method 200 also includes a pathogen inactivation function 224. The pathogen inactivation function 224 receives a treatment-initiated pooled random donor dose 222 (now carried in container 232). Depending upon the functionality of pathogen inactivating compound 218, pathogen inactivation can proceed without further stimulus in the container 232. When further stimulus is required, e.g., light activation, the pathogen inactivation function 224 and subjects the dose 222 to the additional stimulus required in the pathogen inactivation process.

Figure 13:
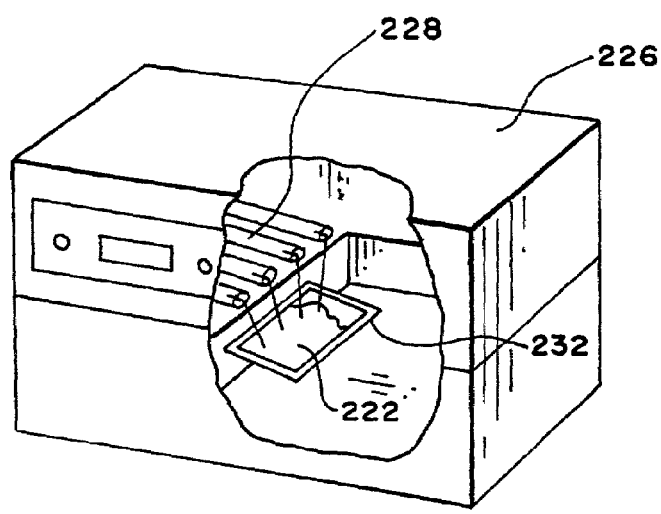
FIG. 13 is a perspective view of a device that performs the function incorporated in the system and method shown in FIG. 11, of pathogen-inactivating a treatment-ready pooled dose of platelet components.

In one embodiment, this function 224 (see FIG. 13) can include placing the treatment-initiated pooled random donor dose 222 (in the container 232) into association with a device 226 having a source of electromagnetic radiation 228. The source 228 provides appropriate wavelengths of electromagnetic radiation to cause activation of the pathogen inactivating compound 218, which, in this arrangement, is photoreactive. The device 226 can support one or more doses 222 in a fixed relationship with the radiation source 228 and otherwise control the operation of the photoinactivation process. Further details of a device that carries out a photoinactivation function is shown in U.S. Pat. No. 5,593,823, which is incorporated herein by reference.

The pathogen inactivation function 224 generates a pathogen-depleted pooled random donor platelet dose 230. Upon removal of residual pathogen inactivating compound 218 (e.g., by exposure to an adsorption medium 234 carried in another transfer container 236 coupled to the container 232 (see FIG. 12)), the pathogen-depleted pooled platelet dose 230 is suited for long term storage and/or transfusion. As FIG. 12 shows, the pathogen-depleted pooled platelet dose 230 can be transferred to a storage container 238, which is coupled to the transfer container 234. As FIG. 12 shows, the in-line container 220 (holding the photoinactivating compound 218), the transfer container 232 (in which pathogen inactivation occurs), the transfer container 236 (where removal of the pathogen inactivating compound 218 occurs), and the storage container 238 (where the pathogen-depleted pooled platelet dose 230 is ultimately stored) can comprise an integrated sterile system 240 that is coupled to a pooling container when it is time to complete the pathogen inactivation process.

Figure 15:
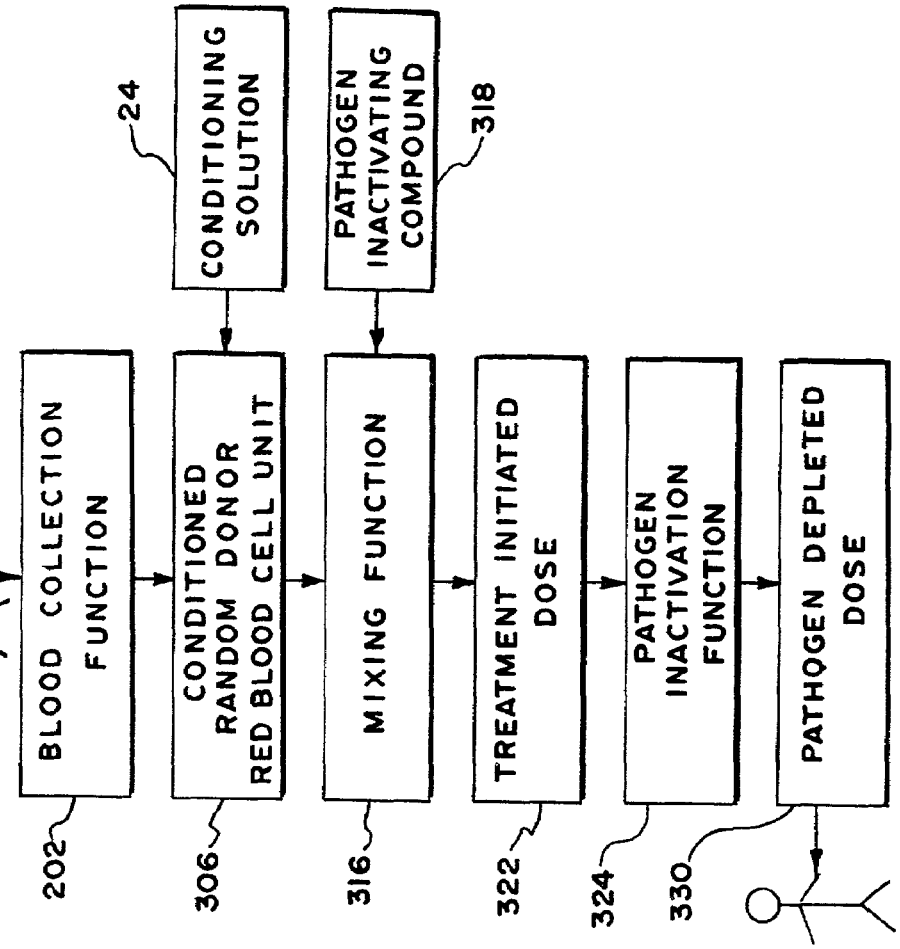
FIG. 15 is a schematic view of a blood processing system and related method that provide red blood cell components harvested in sterile closed systems, which are conditioned for pathogen inactivation.

As FIG. 15 shows, the random donor sterile red blood cell (RBC) unit 208 (which can also have undergone closed system leukocyte filtration) can itself be conditioned by the blood collection function 202 for pathogen inactivation by the mixing, in a sterile, closed system, of a prescribed red blood cell additive solution 24, as previously described (see, e.g., FIG. 1). This provides a random donor sterile red blood cell component unit 306, which is also suited for long term storage in the absence of pathogen inactivation. The function 202 can also have subjected the random donor sterile red blood cell component unit 306 to closed system leukocyte filtration, as previously described (see, e.g., FIG. 5), so that the unit 306 is conditioned for pathogen inactivation and/or long term storage in a leukocyte-reduced state. The conditioning of the red blood cell unit 306 for pathogen inactivation can be performed in combination with conditioning of the platelet concentrate for pathogen inactivation, or alone, without conditioning the platelet component for pathogen inactivation.

In this arrangement, as FIG. 15 also shows, a pathogen inactivating compound mixing function 316 is also provided. The mixing function 316 receives a conditioned red blood cell unit 306 and mixes with it a desired volume of a pathogen inactivating compound 318 for red blood cells. Examples of pathogen inactivating compounds useful in red blood cell pathogen inactivation include the pathogen inactivating compounds disclosed above, as well as those disclosed in U.S. Pat. No. 6,093,725 and pending U.S. patent application Ser. No. 09/539,226, filed Mar. 30, 2000, which is directed to the use of compounds having nucleic acid affinity and containing a mustard group, or mustard group equivalent, or mustard group intermediate. U.S. Pat. No. 6,093,725 and U.S. patent application Ser. No. 09/539,226 are incorporated herein by reference. A preferred pathogen inactivating compound for red blood cell pathogen inactivation is p-alanine, N-(acridin-9-yl), 2-[bis(2-chloroethyl) amino] ethyl ester. The mixing of the red blood cell unit 308 with the compound 318 is desirably accomplished in a sterile fashion, e.g., in the manner like that previously explained in connection with the platelet component dose 214. The mixing function 216 generates a treatment-initiated red blood cell unit 322.

In this arrangement, a pathogen inactivation function 324 receives the treatment-initiated red blood cell unit 322. Depending upon the functionality of pathogen inactivating compound 318, pathogen inactivation can proceed without further stimulus, or with exposure to the additional stimulus that the particular pathogen inactivation process requires. The pathogen inactivation function 324 provides a pathogen-depleted red blood cell unit 330.

Figure 14:
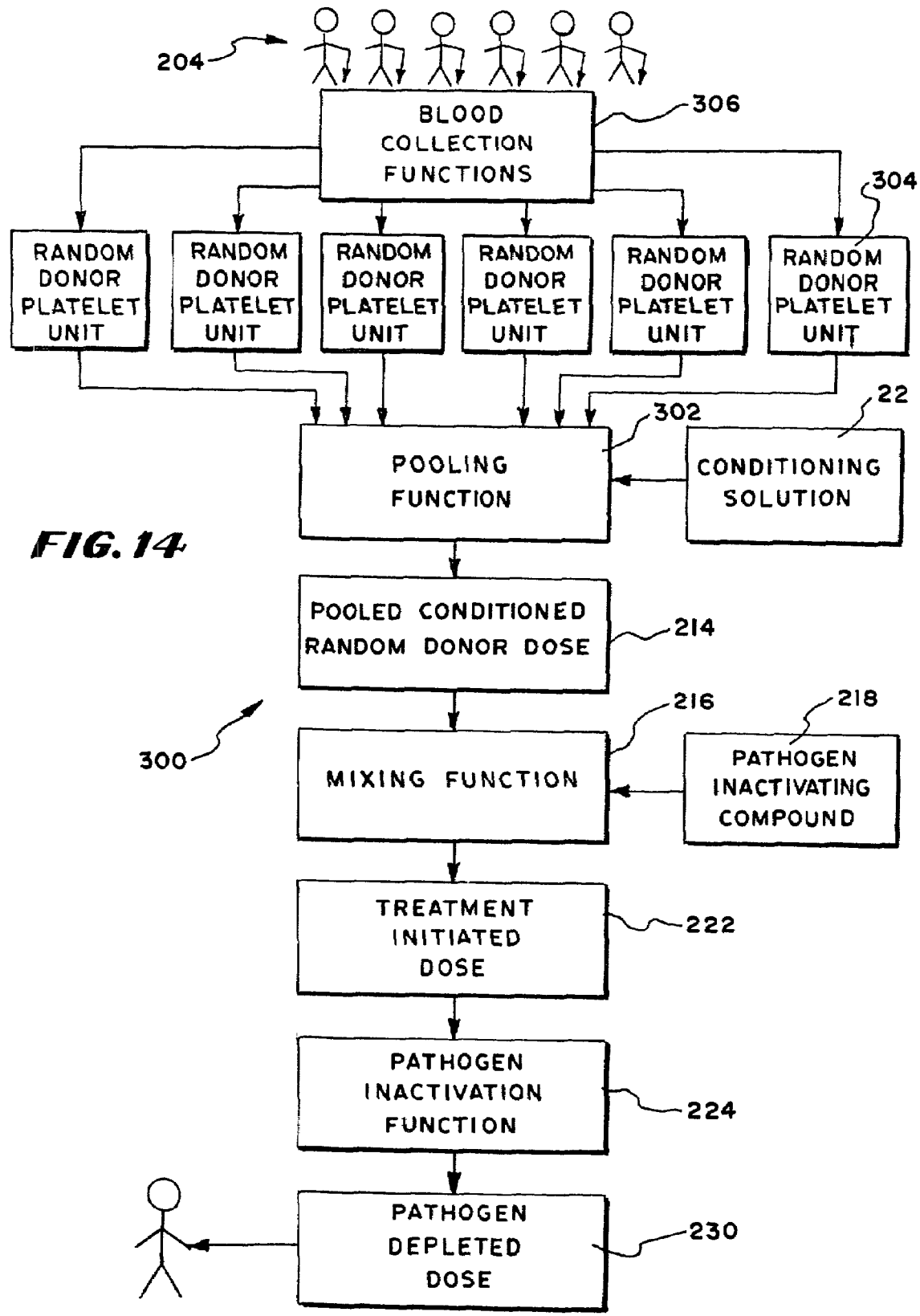
FIG. 14 is a schematic view of another blood processing system and related method that handle platelet components harvested in sterile closed systems as random donor units, and which are conditioned for pathogen inactivation as they are pooled into larger therapeutic doses.

Another system and related method 300 is shown in FIG. 14, which makes possible the conditioning of manually collected random donor platelet units for pooled pathogen inactivation. In FIG. 14, the system and method 300 include a combined pooling and conditioning function 302. The combined function 302 receives a plurality of random donor platelet units 304 generated from individual donors 204 by conventional manual blood processing functions 306 that do not condition the units 304 for pathogen inactivation. The combined function 302 pools these random donor units 304 in a closed system, while at the same time adding the prescribed platelet additive solution 22 to condition them for pathogen inactivation in a pooled state. The function 302 thereby generates a pooled random donor sterile platelet component dose 214, having the same characteristics previously described in connection with the method 200 shown in FIG. 11. The pooling function 302 can comprise the closed, sterile, manually manipulated pooling kits shown in FIG. 6 or 7 or 8 or 9.

The dose 214 generated by the function 302 is conditioned for pathogen inactivation, because the platelet additive solution 22 has been mixed in the act of pooling. The pooled random donor sterile platelet component dose 214 is suited for long term storage in the absence of pathogen inactivation. The function 302 can also have subjected the pooled random donor sterile platelet component dose 214 to closed system leukocyte filtration, so that the dose 214 is conditioned for pathogen inactivation and/or long term storage in a leukocyte reduced state. The function 302 can also have subjected the pooled random donor sterile platelet component dose 214 to closed system centrifugation, so that the dose 214 is essentially free of red blood cells and is conditioned for pathogen inactivation and/or long term storage in this red blood cell-free state.

As FIG. 14 shows, the method 300 can include the subsequent pathogen inactivating compound mixing function 216, to generate a treatment-ready pooled random donor dose 222, and a subsequent pathogen inactivation function 224, to generates a pathogen-depleted pooled random donor platelet dose 230. These functions 216 and 224 and resulting platelet doses 222 and 230, have the same characteristics as those previously described in connection with FIG. 11.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A manual closed blood collection system comprising
    a primary container sized and configured to hold a unit of whole blood drawn from an individual donor for centrifugal separation,
    a platelet unit container downstream of said primary container and sized and configured to hold a platelet concentrate and a first volume of plasma centrifugally separated from the unit of whole blood,
    a plasma unit container sized and configured to hold a second volume of plasma centrifugally separated from the unit of whole blood,
    an auxiliary container downstream of said platelet container,
    a synthetic platelet additive solution carried within the auxiliary container in an at least an amount sufficient for mixing with the platelet concentrate and first volume of plasma to achieve a predetermined ratio of additive solution and plasma and provide a platelet concentrate mixture conditioned for a pathogen inactivation treatment,
    the synthetic platelet additive solution comprising an aqueous solution comprising sodium chloride, sodium citrate, sodium acetate, and sodium phosphate for conditioning the platelet concentrate mixture for pathogen inactivation in the presence of a selected pathogen inactivating compound selected from a group comprising psoralens, methylene blue, dimethyl-methylene blue, riboflavin, or PEN 110, or combinations thereof,
    tubing integrally coupling the primary container, the platelet unit container, the plasma unit container, and the auxiliary container to form a sterile, closed blood processing system,
    an in-line filter adapted to remove leukocytes from separated platelets,
    a filter by-pass branch extending around said filter; and
    a one-way valve provided in said by-pass branch;
    wherein said filter and one-way valve are located between said platelet container and said auxiliary container and allow for direct flow between said platelet and auxiliary containers.

2. A manual blood collection system according to claim 1 wherein, after processing in the sterile, closed blood processing system, the platelet concentrate mixture is held by the platelet unit container.

3. A manual blood collection system according to claim 2 wherein the platelet unit container comprises an appendage coupled to transfer tubing to transfer the platelet concentrate mixture from the platelet unit container to a selected destination.

4. A manual blood collection system according to claim 3 wherein the appendage couples to the transfer tubing to form an essentially sterile connection.

5. The manual closed blood collection system of claim 1 further comprising,
   a) a flow path having one end terminating in a donor needle and another end communicating with an inlet of said primary container;
   b) a flow path having one end communicating with an outlet of said primary container and another end communicating with a first connector;
   c) a flow path having one end communicating with said first connector and another end communicating with a second connector that is downstream of said first connector;
   d) a flow path having one end communicating with said second connector and another end communicating with a third connector that is downstream of said second connector,
   e) wherein said one-way valve and in-line filter are in flow communication with and located between said third connector and said auxiliary container.

* * * * *